United States Patent [19]

Ishiguro et al.

[11] Patent Number: 5,814,447
[45] Date of Patent: Sep. 29, 1998

[54] METHOD OF DETECTING SPECIFIC NUCLEIC ACID SEQUENCES

[75] Inventors: Takahiko Ishiguro, Kanagawa-ken; Masami Otsuka; Teruhiko Inoue, both of Kyoto; Hideo Yawata, Kanagawa-ken; Yukio Sugiura, Kyoto, all of Japan

[73] Assignee: Tosoh Corporation, Shinnanyo, Japan

[21] Appl. No.: 564,650

[22] Filed: Nov. 29, 1995

[30]    Foreign Application Priority Data

Dec. 1, 1994   [JP]   Japan .................................... 6-298665
Jul. 21, 1995  [JP]   Japan .................................... 7-185599

[51] Int. Cl.[6] .............................. C12Q 1/68; C12P 19/34
[52] U.S. Cl. .............................................. 435/6; 435/91.2
[58] Field of Search ...................... 435/6, 91.2; 935/77, 935/78

[56] References Cited

U.S. PATENT DOCUMENTS 4,737,454   4/1988   Dattagupta et al. ...................... 435/6

FOREIGN PATENT DOCUMENTS 0 487 218   5/1992   European Pat. Off. .
0 488 243   6/1992   European Pat. Off. .
0 492 570   7/1992   European Pat. Off. .
0 512 334   11/1992  European Pat. Off. .
2 686 621   7/1993   France .

*Primary Examiner*—Eggerton A. Campbell
*Attorney, Agent, or Firm*—Oblon, Spivak, McClelland, Maier & Neustadt, P.C.

[57] ABSTRACT

A labeled nucleic acid probe comprising a single-stranded oligonucleotide probe having a nucleic acid sequence complementary to a specific nucleic acid sequence in a target nucleic acid and an intercalating fluorochrome bound to said probe is used to detect the target nucleic acid by a convenient, single-stage method in a homogeneous system. The formation of a complementary bond between the probe and the target nucleic acid can be detected and the amount of the resulting complementary binding product determined without requiring any extra step such as for removing the excess probe which has not participated in the complementary binding.

8 Claims, 15 Drawing Sheets

```
TargetType1:
(5')TTTGGGCGTGCCCCC GCAAGACTGCTAGCC(3')
          ||||||   ||#||
YO-271:(3')GTCGGGGG*CGCTC(5')
TargetType2: |||||| |||||
(5')TTTGGGCGTGCCCCC GCGAGACTGCTAGCC(3')
```

Fig. 14

```
SKP/SC1-1:
(5')TTTGGGGCGTGCCCCC  GCAAGACTGCTAGCC(3')
     |||||  ||#||
YO-271: (3')GTCGGGGG*CGCTC(5')
            |||||  |||||
(5')TTTGGGGCGTGCCCCC  GCGAGACTGCTAGCC(3')
SKP/SR1P2-6:
```

METHOD OF DETECTING SPECIFIC NUCLEIC ACID SEQUENCES

BACKGROUND THE INVENTION

This invention relates to a method of detecting a target nucleic acid (i.e., a nucleic acid having a specific nucleic acid sequence) contained in a sample suspected of the presence of a gene mixture. The invention is useful in various gene-related fields including gene diagnosis, the cloning of useful genes and the search for unknown genes. The invention is also useful as a method of optimizing the reaction conditions for a nucleic acid amplifying step.

Detection and quantification of a target nucleic acid rely upon the property of the target nucleic acid to form a complementary bond with a nucleic acid probe having a sequence complementary to a specific nucleic acid sequence, or a specific nucleic acid base sequence, contained in that target nucleic acid.

There has been known a detection method in which a target nucleic acid is sandwiched between two nucleic acid probes comprising sequences capable of forming complementary bonds to specific nucleic acid sequences at different sites in the target nucleic acid. In this method which is commonly referred to as a "sandwich assay" technique, the first of the two nucleic acid probes is immobilized on an insoluble carrier whereas the second nucleic acid probe is labeled in part with dyes or phosphors that have color in the visible range or enzymes capable of producing such dyes or phosphors. When these nucleic acid probes are added to a sample of interest, the target nucleic acid in the sample forms complementary bonds with the first and second nucleic acid probes, thereby forming a complex of the three components on the insoluble carrier. Subsequent to the formation of the complex, the supernatant in the reaction solution is separated from the insoluble carrier by filtration and at least the unreacted second nucleic acid probe that did not participate in the formation of said complex is removed from the reaction solution of the sample (this step is generally referred to as "B/F separation"). Thereafter, the marker in the complex on the insoluble carrier is assayed to determine whether the target nucleic acid is contained in the sample and, if it is present, how much of it is contained.

If an enzyme capable of producing a dye or a phosphor that have color in the visible range is used as a marker for the second nucleic acid probe, a substrate for the enzyme which is a dye or phosphor precursor is added to the reaction solution after the complex formation and the removal of the unreacted second nucleic acid probe and the resulting reaction product such as a dye or phosphor is assayed to determine whether the target nucleic acid is contained in the sample and, if it is present, how much of it is contained.

The use of the insoluble carrier in the sandwich assay technique presents a problem that results from the non-specific adsorption of the second nucleic acid probe onto the insoluble carrier, i.e., at the stage of assaying the marker in the complex on the insoluble carrier, a signal originating from the non-specifically adsorbed second nucleic acid probe enters the result of assaying to cause an error in the detection or the target nucleic acid in the sample or the determination of its amount, thereby introducing difficulty in achieving correct evaluation.

Therefore, with a view to avoiding this problem, attempts have so far been made to reduce the non-specific adsorption of the second nucleic acid probe, such as by rendering the surface of the insoluble carrier used hydrophilic, blocking the sites of adsorption on the carrier surface with proteins or the like, and by thoroughly washing the insoluble carrier after the B/F separation step.

These methods, however, have their own problems. If the insoluble carrier is washed by an increased number of times in the B/F separation step, a prolonged time is necessary to attain the result. Enhancing the efficiency of washing the insoluble carrier by the use of a surfactant in the detergent solution is not practically feasible since there is a likelihood for the accelerated decomposition of the complex formed on the carrier.

The chemical treatment of the carrier surface to render it hydrophilic is not necessarily easy to accomplish from a technical viewpoint since its success depends on the material of which the carrier is made. The approach of covering the carrier surface with a protein or the like to achieve preliminary blocking of the adsorption sites has the disadvantage that the covering material such as proteins may interact with the second nucleic acid probe or its marker to cause another non-specific adsorption.

Thus, the use of the nucleic acid immobilizing insoluble carrier in the "sandwich assay" technique for the purpose of specifically trapping the target nucleic acid has presented fundamental problems to be solved for accomplishing precise detection and quantification of the target nucleic acid in a sample of interest. Under the circumstances, it is required today to develop a single-stage method for the detection of the target nucleic acid in a homogeneous system without using any carriers that involve the aforementioned disadvantages.

A polymerase chain reaction (PCR) method has recently been developed (see Japanese Patent Publication Nos. 67957/1992 and 67960/1992) and it is now possible to amplify nucleic acids under in vitro conditions.

Under the circumstances, it has been proposed that a specific region of a target nucleic acid in a sample of interest be amplified by, with the amplification reaction solution or the like the PCR method and that thereafter being used as a sample, the aforementioned "sandwich assay" technique should be applied, followed by the assay of the amplification product to detect and quantitate the target nucleic acid in the sample before amplification. However, even this approach is not capable of solving the already described fundamental problems with the "sandwich assay" technique and precise measurements have not been attainable.

Another approach that has been proposed on the basis of the amplification of the target nucleic acid by the PCR method comprises the following steps: adding to the amplification reaction solution or the like a nucleic acid probe having a sequence complementary to a specific sequence portion of the target nucleic acid; placing the mixture under conditions that form a complementary bond between the target nucleic acid and the nucleic acid probe; separating the resulting complex from the unreacted nucleic acid probe by a suitable procedure such as electrophoresis; thereafter assaying the marker of the nucleic acid probe, thereby analyzing the amplification product; and determining, on the basis of the result of the analysis, as to whether the target nucleic acid was contained in the sample before amplification and, if it is present, how much of it is contained.

However, each of those assays of the target nucleic acid involving the step of amplification by the PCR method requires that the PCR amplified sample be taken out of the reaction vessel and this only imposes the problem of increased labor and analysis time on the site of clinical diagnosis where efficiency and economy are two important objectives. In addition, the scattering of the amplification product (due to its aerosol) which is held to be a problem with the practical application of the PCR method may potentially cause false positive results, which is indeed a serious problem.

Under these circumstances, the Applicants, noting that the product of amplification by PCR was a double-stranded DNA, employed an intercalating fluorochrome having a certain property such as the tendency to exhibit increased intensity of fluorescence, added it to a sample solution before a specific region of the target nucleic acid was amplified by PCR, and measured the intensity of fluorescence from the reaction solution at given time intervals, thereby detecting and quantitating the target nucleic acid before amplification. The Applicants created a novel method of assaying on the basis of these procedures and filed a patent application on it (see Japanese Patent Public Disclosure No. 237000/1993). According to this method, if the reactor used is made of material that is optically transparent at the excitation and fluorescence wavelengths of the intercalating fluorochrome to be used, the progress of PCR can be monitored from the measurement of the intensity of fluorescence from the reaction solution within the sealed reaction vessel and this eliminates the need to sample successive portions of the reaction solution from within the reaction vessel for analysis, thereby making it possible to avoid the false positive result which would otherwise occur due to the scattering of the amplification product.

The above-described method created by the Applicants has the great advantage of realizing one-stage detection of the target nucleic acid in a homogeneous system without using any carriers. On the other hand, the method involves certain new problems due to the property of the intercalating fluorochrome to be intercalated non-specifically into a double-stranded nucleic acid. Stated more specifically, if the sample contains not only the target nucleic acid but also a large amount of genomic DNA, the intercalating fluorochrome is intercalated into this non-target component and the resulting intense background fluorescence can introduce difficulty in ensuring that the increasing intensity of fluorescence due to the amplification of the target nucleic acid is measured with reasonable precision.

Another problem is associated with the fact that a pair of nucleic acids complementary to the base sequence of the target nucleic acid are used as primers for the extension reaction in PCR. Depending on the selection of the nucleic acid sequence of each primer, the two nucleic acids used as the primers may enter into a complementary binding reaction to form a primer dimer, with one primer being used as a template for the synthesis from the other. The intercalating fluorochrome is also intercalated non-specifically into the primer dimer and the resulting increase in the intensity of background fluorescence can be a great obstacle to the monitoring of the time-dependent change in the intensity of fluorescence due to the amplification of the target nucleic acid to be assayed.

To deal with this problem, it is necessary that the intercalating fluorochrome under consideration be given a specificity that enables it recognize a specific nucleic acid sequence.

The present invention has been accomplished with a view to solving the aforementioned problems of the prior art and its primary objective is to provide a convenient one-stage method in a homogeneous system by which a target nucleic acid, or a nucleic acid in a sample of interest that has at least one specific nucleic acid sequence, can be detected and quantitated in high precision without the need to separate excess part of the labeled nucleic acid probe which has not contributed to the occurrence of complementary binding in the conventional "sandwich assay" technique or the like and without causing any unwanted phenomena such as an increased intensity of background fluorescence during amplification by PCR or other procedures. The method is useful in various gene-related fields such as gene diagnosis, the cloning of useful genes and the search for unknown genes, as well as for the purpose of optimizing the reaction conditions for a nucleic acid amplifying step.

SUMMARY OF THE INVENTION

The present inventors conducted intensive studies in order to attain the above-stated object and successfully accomplished the present invention. The method provided by the invention is for detecting a specific nucleic acid, more particularly for assaying a target nucleic acid, or a nucleic acid in a sample of interest that has at least one specific nucleic acid sequence and it uses as a probe a single-stranded oligonucleotide having a nucleic acid sequence complementary to said specific nucleic acid sequence in the target nucleic acid and includes the step of adding said probe to the sample such as to form a complementary bond with the target nucleic acid; the method is characterized in that said probe is a single-stranded oligonucleotide labeled with an intercalating fluorochrome which is to be intercalated into the complementary binding portion between the target nucleic acid and the single-stranded oligonucleotide probe.

If the target nucleic acid is a double-stranded nucleic acid, nucleic acid probes can effect complementary binding with the target nucleic acid to form triple-stranded nucleic acids. Thus, the present invention also provides a method of assaying a target nucleic acid, or a double-stranded nucleic acid in a sample of interest that has at least one specific nucleic acid sequence, which uses as a probe a single-stranded oligonucleotide having a nucleic acid sequence complementary to said specific nucleic acid sequence in the target nucleic acid and which includes the step of adding said probe to the sample such as to form a triple-stranded nucleic acid with the target nucleic acid; the method is characterized in that said probe is a single-stranded oligonucleotide labeled with an intercalating fluorochrome which is to be intercalated into the triple-stranded portion formed from the target nucleic acid and the single-stranded oligonucleotide probe.

According to a second aspect, the present invention provides a labeled nucleic acid probe for detecting a single- or double-stranded target nucleic acid having a specific nucleic acid sequence, said probe comprising a single-stranded oligonucleotide probe having a nucleic acid sequence complementary to said specific nucleic acid sequence and an intercalating fluorochrome; the probe is characterized in that the intercalating fluorochrome is bound to the single-stranded oligonucleotide probe in such a way that it can be intercalated into the complementary binding portion formed by complementary binding between the single-stranded target nucleic acid and the single-stranded oligonucleotide probe or the triple-stranded portion formed from the double-stranded target nucleic acid and the single-stranded oligonucleotide probe.

According to a third aspect, the present invention provides a method of detecting a specific nucleic acid sequence by assaying a target nucleic acid, or a nucleic acid in a sample of interest that has at least one specific nucleic acid sequence, which method includes the step of amplifying at least said specific nucleic acid sequence portion by a polymerase chain reaction (PCR) method or some other suitable method, uses as a probe a single-stranded oligonucleotide having a nucleic acid sequence complementary to said specific nucleic acid sequence in the target nucleic acid and further includes the step of adding said probe to the sample such as to form a complementary bond with the target nucleic acid; the method is characterized in that said probe is a single-stranded oligonucleotide labeled with an intercalating fluorochrome which is to be intercalated into the complementary binding portion between the target nucleic acid and the single-stranded oligonucleotide probe.

As already mentioned, nucleic acid probes are capable of forming triple-stranded nucleic acids by complementary binding with the target nucleic acid even if it is a double-stranded nucleic acid. Thus, the present invention also provides a method of assaying a target nucleic acid, or a double-stranded nucleic acid in a sample of interest that has at least one specific nucleic acid sequence, which method includes the step of amplifying at least said specific nucleic acid sequence portion by the polymerase chain reaction (PCR) method or some other suitable method, uses as a probe a single-stranded oligonucleotide probe having a nucleic acid sequence complementary to said specific nucleic acid sequence in the target nucleic acid and further includes the step of adding said probe to the sample such as to form a hybridization with the target nucleic acid; the method is characterized in that said probe is a single-stranded oligonucleotide labeled with an intercalating fluorochrome which is to be intercalated into the triple-stranded portion formed from the target nucleic acid and the single-stranded oligonucleotide probe.

BRIEF DESCRIPTION OF THE DRAWINGS

FIG. 14 shows how SKP/SC1-1 and SKP/SR1P2-6, the clones prepared in Example 7, formed double strands with YO-271;

DETAILED DESCRIPTION OF THE INVENTION

Figure 1:
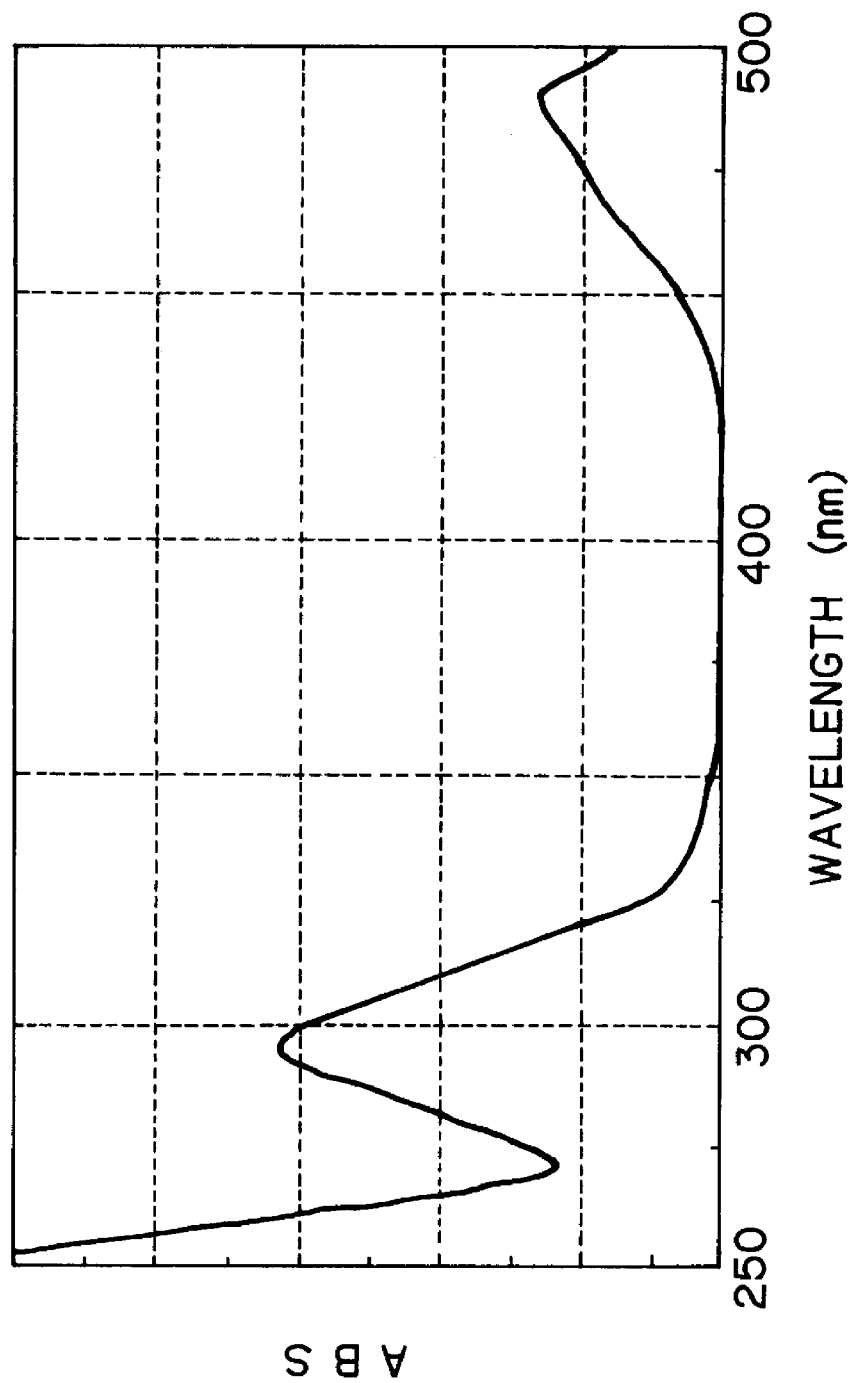
FIG. 1 is a graph showing the absorption spectrum of YO-PU-1, a labeled nucleic acid probe for use in the invention.

In accordance with the invention which uses a heretofore unknown nucleic acid probe, a target nucleic acid can be detected without the need to separate excess part of the labeled nucleic acid probe which has not contributed to the occurrence of complementary binding in the conventional "sandwich assay" technique or the like and without causing any unwanted phenomena such as an increased intensity of background fluorescence during amplification by PCR or other methods. Stated more specifically, the labeled nucleic acid probe to be used in the invention consists of a single-stranded oligonucleotide portion having affinity for the target nucleic acid, the label portion consisting of an intercalating fluorochrome and an optional linker portion that may be incorporated to couple those two portions. The intercalating fluorochrome is intercalated into the complementary binding portion or the triple-stranded portion which are formed from the target nucleic acid and the probe and the intercalated fluorochrome will experience certain changes in its fluorescence characteristic. On the basis of these changes in the fluorescence characteristics of the intercalating fluorochrome, one can detect and quantitate the nucleic acid which is contained in the sample and which consists of a specified base sequence.

The labeled nucleic acid probe that is provided by the present invention for use in detecting the target nucleic acid comprises a single-stranded oligonucleotide probe and an intercalating fluorochrome. The single-stranded oligonucleotide probe has preferably a nucleic acid sequence having 100% complementarily with the specific nucleic acid sequence in the target nucleic acid; however, a partial base mismatch is allowed for if it is not detrimental to the specificity and complementarily of the probe. The "specific nucleic acid sequence" is a base sequence of a certain length, say, about 10–30 bases, preferably about 15–25 bases. It is particularly preferred that the specific nucleic acid sequence occurs only in the target nucleic acid and is not detectable in other nucleic acids, thus providing for distinction from such other nucleic acids. However, the "specific nucleic acid sequence" need not necessarily be the one that occurs only in the target nucleic acid and any sequence will suffice if it is reasonably "specific" with respect to other nucleic acids that are suspected to be present in the sample. Therefore, the labeled nucleic acid probe of the invention may appropriately be selected from among those having a length corresponding to the already defined "specific nucleic acid sequence", i.e., about 10–30 bases, preferably about 15–25 bases, in association with the target nucleic acid. In the case of applying the present invention to the detection of a double-stranded nucleic acid by taking advantage of the ability of the oligonucleotide probe to enter into a complementary binding reaction with a double-stranded nucleic acid, either one of the two strands needs only to have a specific nucleic acid sequence. Needless to say, it is within the scope of the invention to set more than one "specific nucleic acid sequence" and use the corresponding number of labeled nucleic acid probes.

The intercalating fluorochrome that may be used in the invention is not limited to any material as long as it is intercalated into a double- or triple-stranded nucleic acid, experiencing certain changes in its fluorescence characteristics compared to the case where it is in the free state. Various intercalating fluorochromes can be used in the invention and they include: fluorochromes such as Acridine Orange, Thiazole Orange and Oxazole Yellow which, when intercalated, are subject to significant changes primarily in the intensity of their fluorescence; fluorochromes which are subject to changes primarily in the absorption spectrum of exciting light; fluorochromes such as bis-bentimide which are subject to changes primarily in the peak wavelength of radiation spectrum; and fluorochromes which are subject to changes primarily in both the absorption spectrum of exciting light and the peak wavelength of radiation spectrum. While any of these fluorochromes may be used, those which are subject to significant increases in the intensity of fluorescence upon intercalation are used with particular preference from practical viewpoints such as the ease of detection. Such particularly preferred intercalating fluorochromes may be exemplified by Thiazole Orange and Oxazole Yellow.

The intercalating fluorochrome binds to the aforementioned single-stranded oligonucleotide probe by, for example, covalent bonding. If desired, a linker of an appropriate molecular length may be interposed. Any molecule may be used as a linker if it does not prevent the intercalating fluorochrome from being intercalated into the complementary binding portion formed of the single-stranded oligonucleotide probe and the target nucleic acid, or in the triple-stranded portion that is formed of the single-stranded oligonucleotide probe and a double-stranded nucleic acid as the target nucleic acid. The use of a bifunctional hydrocarbon having a functional group at both terminals may be mentioned as an advantageous example from practical viewpoints such as the ease of binding operations. If desired, a commercial reagent such as C6-Thiol modifier available from Clontech Inc. may be employed as the linker.

The labeled nucleic acid probe according to the present invention may also be used to detect a double-stranded target nucleic acid. In this case, the nucleic acid probe enters into a specific complementary binding reaction with a specific nucleic acid in one of the two strands of the double-stranded nucleic acid, producing a nucleic acid which is triple-stranded, at least in part. In the case under consideration, the intercalating fluorochrome is intercalated not only into the complementary binding portion formed from the nucleic acid probe and the nucleic acid having the specific nucleic acid sequence but also in the complementary binding portion formed by the target nucleic acid and, therefore, the linker to be used in this case is preferably one having a comparatively extended molecular length.

The intercalating fluorochrome may bind to the single-stranded oligonucleotide probe at any site as long as it does not interfere with the intercalation of the fluorochrome or the complementary binding of the labeled nucleic acid probe to the target nucleic acid. The binding site may be at the 5' or 3' terminal of the probe or in its central portion but the 5' or 3' terminal is particularly preferred. As will be described later in this specification, if PCR is to be performed in the presence of the labeled nucleic acid probe of the invention and if said probe is allowed to function as a primer for PCR, the intercalating fluorochrome is preferably bound to the 5' terminal of the probe so as to insure that it will not retard the reaction of nucleic acid extension with a DNA synthetase.

If the thus prepared labeled nucleic acid probe of the invention forms a complementary bond with the target nucleic acid, the intercalating fluorochrome which is bound to said probe will be intercalated into the complementary binding portion or the triple-stranded portion and this causes various changes in the fluorescence characteristics of the fluorochrome, such as an increased intensity of fluorescence. This makes it possible to detect the formation of a complementary bond if any and to quantify the complementary binding product that has formed and yet there is no need to separate excess part of the probe that did not contribute to the complementary binding reaction. Therefore, using the labeled probe of the invention, one can detect the target nucleic acid having a specific nucleic acid sequence by a convenient, one-stage method a homogeneous system.

The labeled probe of the invention having the aforementioned features will prove reasonably effective even if it is used in the conventional "sandwich assay" technique employing an insoluble carrier because several advantages result, as exemplified by the elimination of the step of separating the excess portion of the probe. However, the most important feature of the labeled probe of the invention is that it enables the target nucleic acid to be detected by a convenient one-stage method in a homogeneous system and, as will be apparent from the foregoing description, one can detect the target nucleic acid by merely adding the probe to a sample of interest.

The present invention also provides the novel use of the labeled nucleic acid probe in a method of assaying the target nucleic acid which includes the step of amplifying at least a specific nucleic acid sequence portion of the target nucleic acid by a suitable technique such as PCR and which uses as a probe a single-stranded oligonucleotide having a nucleic acid sequence complementary to the specific nucleic acid sequence in the target nucleic acid and which further includes the step of adding the probe to the sample such as to form a complementary bond with the target nucleic acid.

According to PCR and other amplification procedures, the very small amount of the target nucleic acid in the sample can be amplified by a factor of at least several thousand and, hence, the presence of a target nucleic acid that could not be detected by ordinary procedures (which do not utilize PCR or any other amplification techniques) can be detected and, what is more, the quantity of the resulting complementary binding product can be determined. The application of the PCR-based detection method of the invention is particularly preferred for the purpose of detecting nucleic acids that derive from pathogenic viruses such as human immunodeficiency virus and hepatitis C virus and that occur in very small amounts.

The application of the present invention to a method of assaying a target nucleic acid after amplifying it by PCR will now be described in detail but it should be understood that the procedure of amplifying the target nucleic acid is by no means limited to PCR and other procedures may be employed such as LCR. It should also be noted that the procedure of introducing the target nucleic acid into a suitable cell so as to express mRNA may effectively be regarded as the step of amplifying the target nucleic acid. Therefore, the concept of the invention is also applicable to these non-PCR amplification procedures as will be described just below.

The procedure of the PCR method per se is well known and may be implemented by referring to prior patents such as Japanese Patent Publication Nos. 67957/1992 and 67960/1992, supra.

The PCR-based detection method of the invention starts with adding the labeled nucleic acid probe of the invention to a sample of interest before a specific nucleic acid sequence portion of the target nucleic acid in the sample is amplified by PCR. Then, PCR is performed by temperature cycling or some other suitable technique in the presence of the probe in a sealable reaction vessel made of a material that is optically transparent at, for example, the excitation and fluorescence wavelengths of the intercalating fluorochrome in the probe. Based on the intensity of fluorescence from the reaction solution within the sealed reaction vessel, one can monitor how the target nucleic acid is amplified over time and he can also check for the presence of the target nucleic acid in the sample while determining the quantity of any complementary binding product that has been formed. As a result, the need to sample successive portions of the reaction solution from within the reaction vessel for analysis is eliminated, thereby making it possible to avoid the false positive results which would otherwise occur due to the scattering of the amplification product.

In the PCR-based method of the invention for detecting the target nucleic acid, the labeled nucleic acid probe can be used as a primer in PCR. Therefore, once the labeled nucleic acid probe has been prepared and is available, one can detect the same target nucleic acid by selectively using the PCR-based and non-PCR based procedures.

If desired, the PCR-based method of the invention for detecting the target nucleic acid may be practiced without using the labeled nucleic acid probe as a primer in PCR. In this case, the labeled nucleic acid probe need be modified to insure that it will not function as a primer, namely to retard the progress of the reaction for nucleic acid extension with a DNA synthetase. To this end, the binding site of the intercalating fluorochrome may be introduced at the 3' terminal of the labeled nucleic acid probe toward which the extension reaction will proceed in PCR or the 3' terminal may be subjected to an appropriate chemical modification so as to insure that the aforementioned extension reaction will not take place. While various methods of chemical modification can be used, a base that will not form a complementary bond with the target nucleic acid may deliberately be introduced at the 3' terminal of the labeled nucleic acid probe and this method is convenient and hence preferred. At least one such base that will not form a complementary bond with the target nucleic acid will suffice for achieving the intended result.

Another advantage of using the labeled nucleic acid probe of the invention is that the appropriate cycle number and other reaction conditions for the step of nucleic acid amplification by PCR can easily be optimized. The use of the labeled nucleic acid probe of the invention also enables the detection of a base variation such as mutation that may have occurred in the nucleic acid sequence. Stated more specifically, the labeled nucleic acid probe of the invention will readily enter into a complementary binding reaction with the target nucleic acid, particularly with great ease in the case where it is single-stranded and this causes certain changes in the fluorescence characteristics of the marker, or the intercalating fluorochrome. Therefore, if a fluorescence characteristic is found to change at a lower temperature than the point where such change would occur in the absence of mutation or a like phenomenon, one may well conclude that mutation or the like did occur in the nucleic acid of interest, causing a change in the stability of the double-stranded nucleic acid it forms. Alternatively, the change in a fluorescence characteristic that occur at a selected temperature may be measured and the result is compared with the reference to determine whether mutation or a like phenomenon occurred in the nucleic acid of interest. A particularly preferred example of this approach is to check against the relative change in a certain fluorescence characteristic that occurs at the temperature (Tm) where 50% of the double-stranded nucleic acid separates into individual single strands.

The following examples are provided for the purpose of further illustrating the present invention but they are given here for illustrative purposes only and are by no means intended to be limiting.

EXAMPLE 1

Preparation of Labeled Nucleic Acid Probe

A labeled nucleic acid probe according to the invention was prepared by the following procedure. A mixture of compound 1 (see the reaction scheme below; 7.56 g, 50 nm), methyl iodide (6.25 ml, 100 mmol), potassium carbonate (3.82 g, 100 mmol) and acetate was refluxed for 2 h and the reaction mixture was left to cool to room temperature. Thereafter, the insolubles were filtered off and the filtrate was concentrated under vacuum. Methylene chloride was added to the residue, the insolubles were filtered off and the filtrate was concentrated under vacuum. Subsequent distillation gave a yellow oil (Compound 2 in the reaction scheme below) in an amount of 6.83 g (yield: 82.3%). Compound 2 showed a signal for the δCH$_3$ group at δ=2.73 in $^1$H NMR (CDCl$_3$).

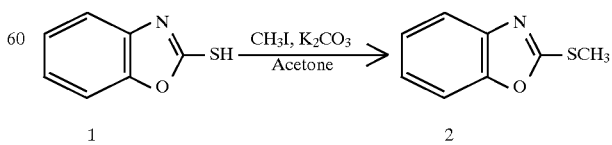

Compound 3 (see the reaction scheme below; 0.856 g, 5.98 mmol) and 1,3-diode propane (5.38 g, 29.9 mmol) were heated at 110° C. for 20 h. The reaction mixture was left to cool to room temperature, followed by the addition of a mixture of hexane and ether. The precipitating yellow solids (Compound 4 in the reaction scheme below) were collected by filtration to give a mass weighing 2.36 g (yield: 96.7%). Compound 4 showed signals for three methylene groups in —CH$_2$CH$_2$CH$_2$I at δ=2.67, 3.46 and 5.45, as well as a signal for the CH$_3$ group at δ=3.03 in $^1$H NMR (CDCl$_3$).

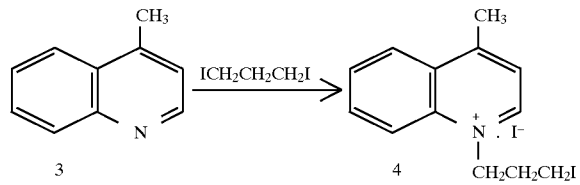

Methyl paratoluenesulfonic acid (1116 mg, 6 mmol) was added to Compound 2 (990 mg, 6 mmol) and the mixture was heated at 110° C. for 5 h, whereupon Compound 7 (see the reaction scheme below) formed. The reaction vessel containing Compound 7 was left to cool to room temperature and, thereafter, Compound 4 (26.34 mg, 7.5 mmol) was added, followed by refluxing at 90° C. for 1 h. Subsequently, the reaction solution was left to cool to room temperature, the insolubles were filtered off and the filtrate was concentrated under vacuum. Methanol was added to the residue and the precipitating yellow solids (Compound 8 in the reaction scheme below) were collected by filtration to give a mass weighing 512 mg (yield: 29.9%). Compound 8 showed a signal characteristic of methine at δ=5.95 in NMR (CDCl$_3$/CD$_3$OD).

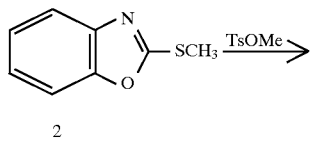

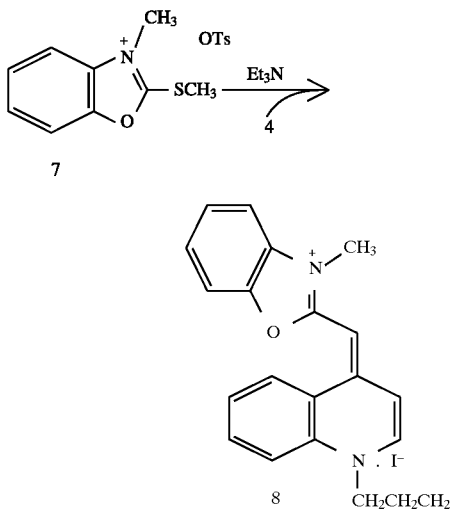

In a separate step, a nucleic acid having the sequence (5')AGAGGGAGAGGAAAA(3') was synthetized as a probe oligonucleotide by means of a DNA synthesizer (391DNA Synthesizer of Applied Biosystems Inc.) and a commercial linker (C$_6$-Thiol Modifier of Clontech Inc.; Catalog No. 5211-1) was bound to this oligonucleotide. The resulting linker-bound oligonucleotide is represented by the following formula, in which Oligomer designates the synthesized nucleic acid (5')AGAGGGAGAGGAAAA(3'):

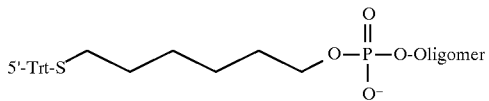

A solution of this oligonucleotide was prepared as follows: 3–5 OD (A$_{260}$) of the above oligonucleotide was dried and dissolved again in 40 µl of 0.1M TEAA (pH 7.5); followed by the addition of 7.5 µl of 1.0M AgNO$_3$, the solution was stirred on a vortex and incubated at room temperature for 40 min. Subsequently, 10 µl of 1.0M DTT was added and the mixture was stirred on a vortex, followed by incubation at room temperature for 30 min. Thereafter, centrifugation was conducted for 15 min and the supernatant was recovered. To the precipitate, 40 µl of 0.1M TEAA (pH 7.5) was added and the mixture was stirred on a vortex and centrifuged for 5 min. The resulting supernatant was combined with the first recovered supernatant to give Compound 9 (see the reaction scheme below) in a total amount of 97.5 µl.

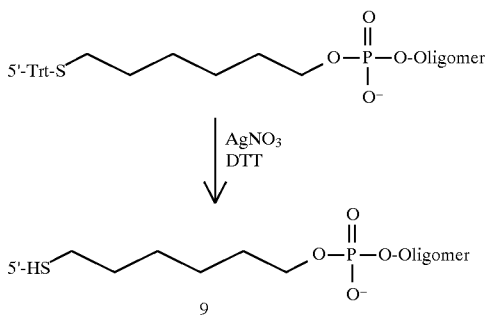

In the next step, 200 µl of DMF, 300 µl of a phosphate buffer solution (pH 10.0) and 500 µl of H$_2$O were mixed and Compound 8 was added to the mixture to form a saturated solution. Thereafter, the reaction atmosphere was replaced by argon gas. In a separate step, a solution of compound 9 that had been purified by high-performance liquid chromatography was mixed with 20 µl of 0.1M DTT and the mixture was stirred on a vortex, followed by replacement with argon gas. The two solutions were mixed in such amounts that the ratio of the solution of Compound 9 to that of Compound 8 was within the range from 2:1 to 3:1. The mixture was left to stand for 2 h and subjected to gel filtration with Sephadex G-25. The filtration product was dried and purified by high-performance liquid chromatography to yield Compound 10 (see the reaction scheme below) which was a labeled nucleic acid probe of the invention (hereunder designated as "YO-PU-1") containing the intercalating fluorochrome (Compound 8, or Oxazole Yellow represented by 3-methyl-2-[[1-[3-iodopropyl]-1,4-dihydroquinolin-4-ylidene]methyl]benzo-1,3-oxazolium iodide). The buffer solution used in the procedure of high-performance liquid chromatography was 0.1M TEAA (pH. 7.0)/50% acetonitrile, and the buffer solution used in the procedure of gel filtration with Sephadex G-25 was 0.1M TEAA (pH 7.0)/5% acetonitrile.

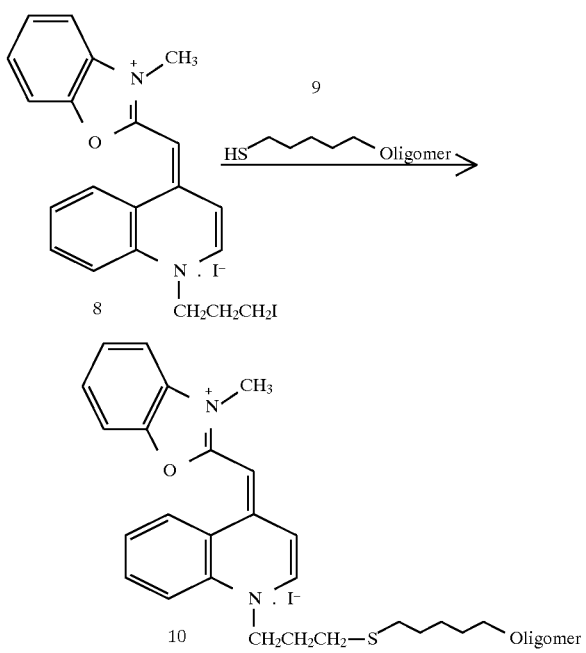

The thus prepared labeled nucleic acid probe (YO-PU-1) of the invention had a UV spectrum as depicted in FIG. 1, which obviously shows two absorption peaks, one derived from the nucleic and the other from Compound 8.

EXAMPLE 2

Experiment 1 for Detection of Target Nucleic Acid

Using the YO-PU-1 prepared in Example 1, an experiment was conducted to detect a target nucleic acid. The target nucleic acid was DS1 having the following nucleic acid sequence, which was synthesized with a DNA synthesizer (391DNA Synthesizer of Applied Biosystems Inc.):

DS1: (5')TTTTCCTCTCCCTCT(3')

A portion (30 pmol) of YO-PU-1 was dissolved in 0.6 ml of 0.2M Tris-HCl (pH 7.5) and the intensity of fluorescence at 510 nm from the solution was measured at room temperature with excitation at 480 nm; the result was 8.2.

In a separate step, 30 pmol of YO-PU-1 and 45 pmol of the target nucleic acid DS1 were dissolved in 2.5 μl of 20x SSC and 50 μl of $H_2O$ and the solution was heated to 90° C., then left to cool to room temperature. Subsequently, 60 μl of 0.2M Tris-HCl (pH 7.5) and 490 μl of $H_2O$ were added and the intensity of fluorescence at 510 nm from the solution was measured, with excitation at 480 nm. The result was 17.0, verifying a significant increase in the intensity of fluorescence over 8.2.

Figure 2:
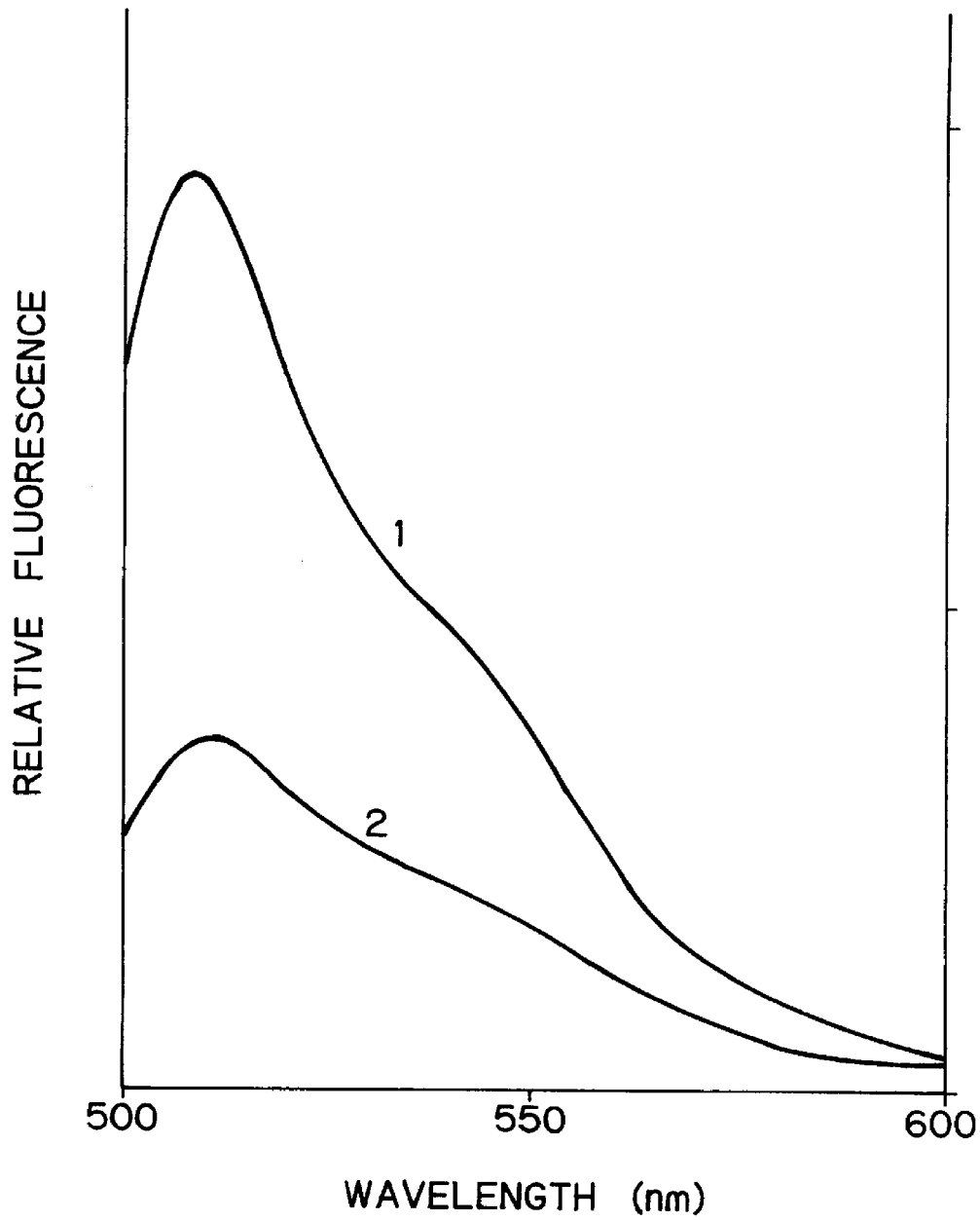
FIG. 2 shows the fluorescence spectrum of an aqueous solution comprising YO-PU-1 and a target nucleic acid DS1, as measured under complementary bond forming conditions (curve 1), as well as the fluorescence spectrum of an aqueous solution of YO-PU-1 (curve 2)

The measured fluorescence spectra are shown in FIG. 2.

In a separate step, 45 pmol of (5')TCGAGCCCATAAA AGGAGAGGGAGATTCCCCTGCC(3'), a nucleic acid comprising a nucleic acid sequence non-complementary to YO-PU-1 (i.e., which did not contain a complementary nucleic acid sequence) and 30 pmol of YO-PU-1 were dissolved in 2.5 μl of 20x SSC and 50 μl of $H_2O$, and the solution was heated to 90° C., then left to cool to room temperature. Subsequently, 60 μl of 0.2M Tris-HCl (pH 7.5) and 490 μl of $H_2O$ were added. The intensity of fluorescence from the resulting solution was measured to be 8.5.

The above results show the following: YO-PU-1 formed a complementary bond only with DS1 which had a nucleic acid sequence complementary to the nucleic acid sequence of that probe; and the intensity of fluorescence was significantly increased as a result of intercalation of the bound intercalating fluorochrome into the complementary binding portion. It was thus verified that the specific nucleic acid in the sample could be detected by merely adding the labeled nucleic acid probe of the invention to the sample.

EXAMPLE 3

Experiment 2 for Detection of Target Nucleic Acid

YO-PU-1 (30 pmol) and 0.1, 0.2, 0.5, 1.0 or 1.5 eq. of the target nucleic acid DS1 were annealed as in Example 2 and the intensities of fluorescence (510 nm) at the respective concentrations of the target nucleic acid were measured at room temperature with excitation at 480 nm.

Figure 3:
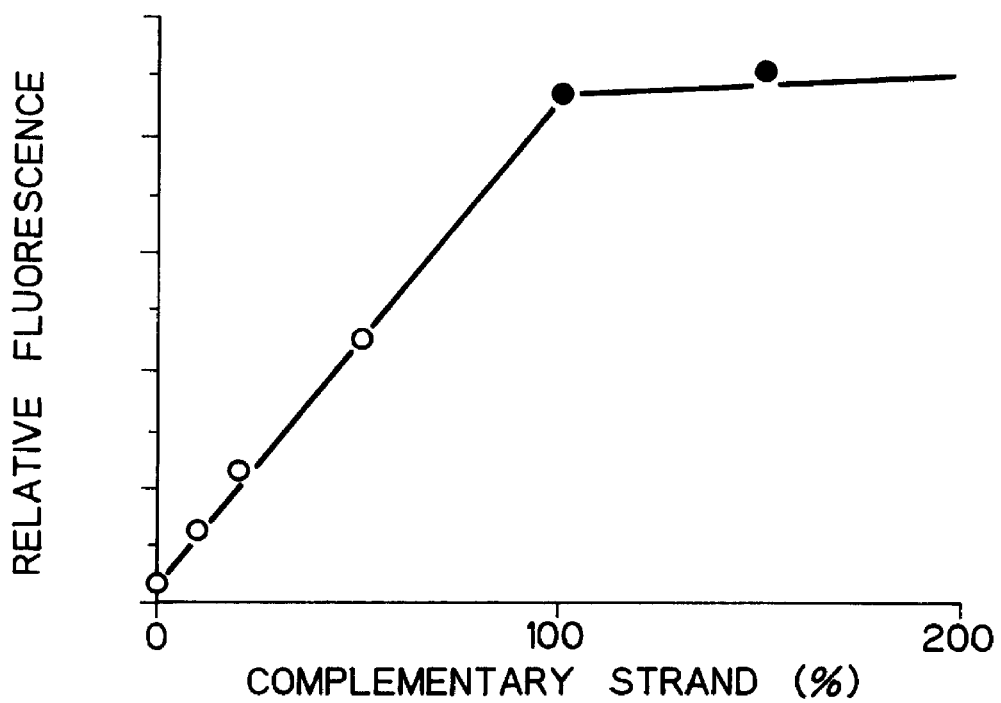
FIG. 3 is a graph showing the intensities of fluorescence from reaction solutions comprising 30 pmol of YO-PU-1 and varying amounts of DS1.

The results are shown in FIG. 3, from which one can see that the intensity of fluorescence from the reaction solution increased in proportion to the amount of the target nucleic acid in the sample. It was thus verified that the amount (concentration) of the specific nucleic acid in the sample could be determined by merely measuring the intensity of fluorescence from the labeled nucleic acid probe added to the sample.

EXAMPLE 4

Experiment 3 for Detection of Target Nucleic Acid

The following target nucleic acid DS2 was synthesized with a DNA synthesizer (391DNA Synthesizer of Applied Biosystems Inc.):

DS2; (5')TTTTCCTCTCCCTCTCCCC(3')

YO-PU-1 (30 pmol) and 0.1, 0.2, 0.5, 1.0 or 1.5 eq. of the target nucleic acid DS2 were annealed as in Example 2 and the intensities of fluorescence (510 nm) at the respective concentrations of the target nucleic acid were measured at room temperature with excitation at 480 nm.

Figure 4:
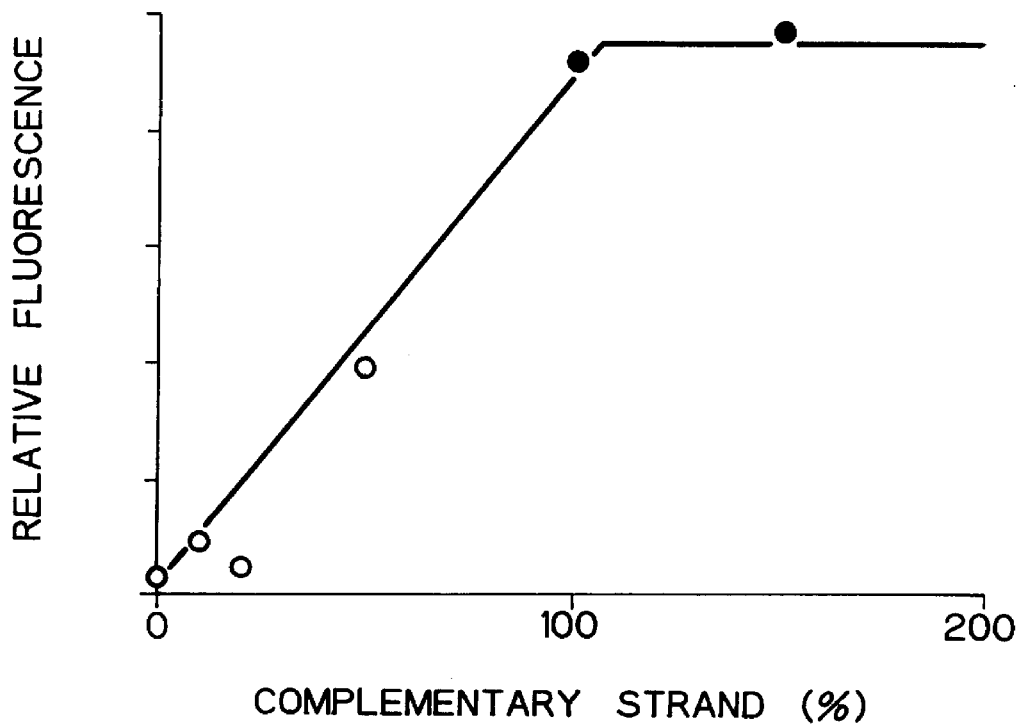
FIG. 4 is a graph showing the intensities of fluorescence from reaction solutions comprising 30 pmol of YO-PU-1 and varying amounts of another target nucleic acid, DS2.

The results are shown in FIG. 4, from which one can see that the intensity of fluorescence from the reaction solution increased in proportion to the amount of the target nucleic acid in the sample. It was thus verified that the amount (concentration) of the specific nucleic acid in the sample could be determined by merely measuring the intensity of fluorescence from the labeled nucleic acid probe added to the sample.

EXAMPLE 5

Preparation of YO-271

Figure 5:
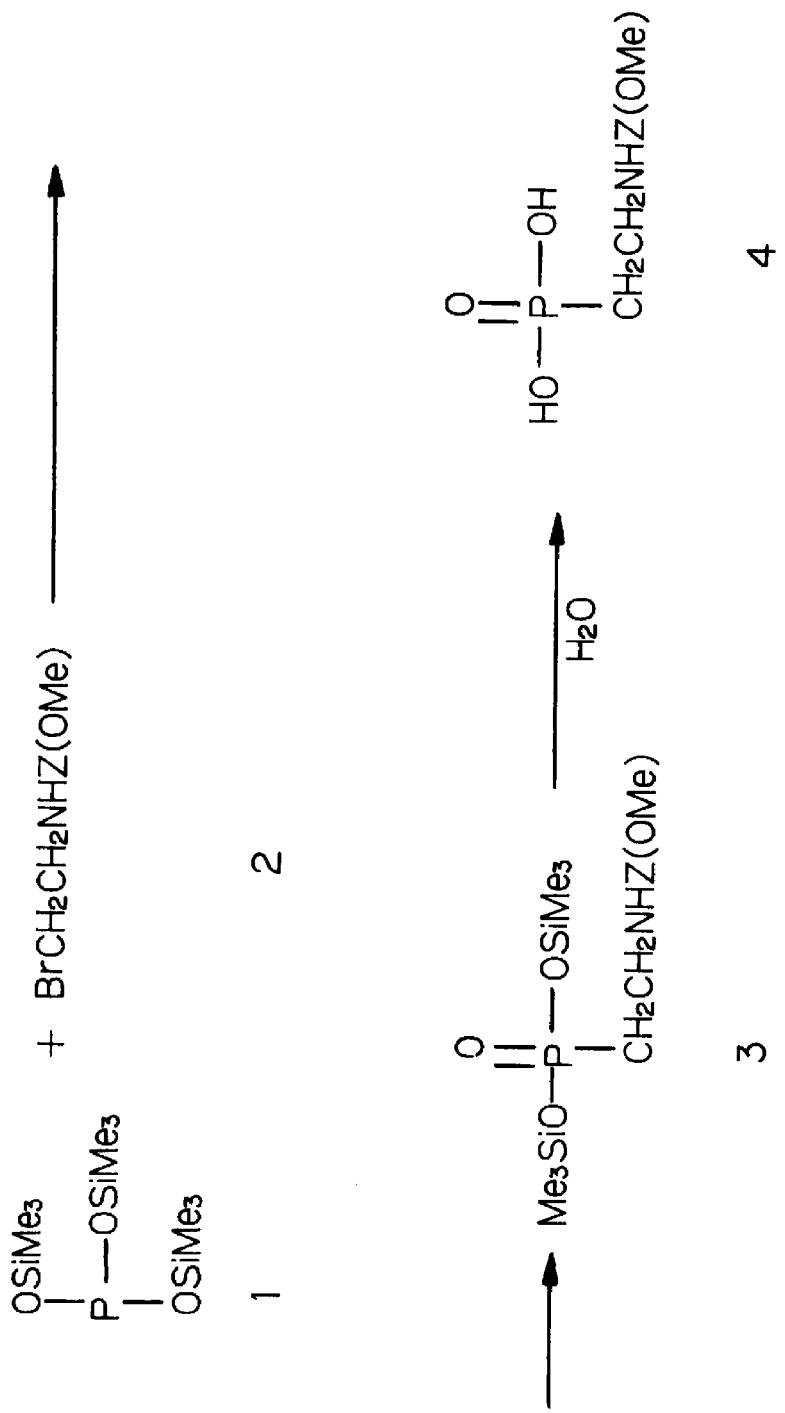
FIG. 5 shows a reaction scheme for the first stage of the preparation in Example 5 of YO-271, another labeled nucleic acid probe for use in the invention.

A reaction was carried out in accordance with the scheme shown in FIG. 5: Compound 1 (10 mmol) was mixed with Compound 2 (10 mmol) and the mixture was heated at 150° C. for 3 h to produce Compound 3 by the Arbusov reaction; thereafter, Compound 3 was hydrolyzed to give Compound 4 in a yield of 70%. In the scheme shown in FIG. 5, Z(OMe) designates a protective paramethoxybenzyloxycarbonyl group:

Deoxynucleotide is generally represented by formula 7:

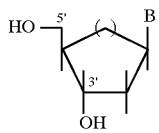

which is hereunder abbreviated as formula 8:

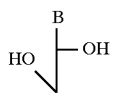

where B signifies any one of the bases adenine (A), guanine (G), cytosine (C), thymine (T) and uracil (U).

Figure 6:
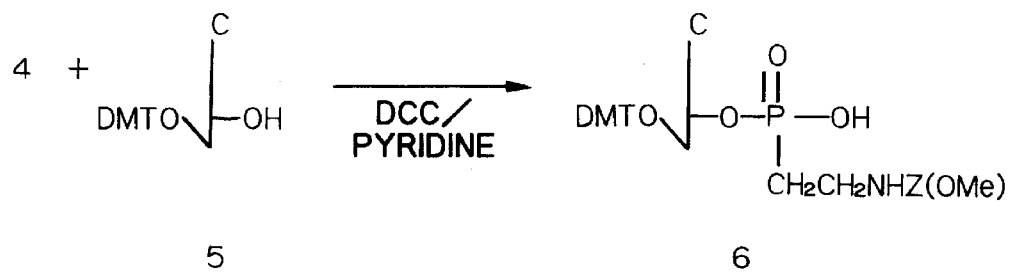
FIG. 6 shows a reaction scheme for the second stage of the preparation of YO-271 in Example 5.

In accordance with the reaction scheme shown in FIG. 6, Compound 4 (7 mmol) and Compound 5 (7 mmol) were dissolved in 70 ml of dry pyridine and 35 mmol of DCC (dicyclohexylcarbodiimide) was added to the solution, which was subjected to reaction at 45° C. for a day; the resulting dicyclohexylurea was filtered off the reaction solution to give Compound 6 (yield: 60%). In the scheme shown in FIG. 6, DMT designates a protective dimethoxytrityl group.

Figure 7:
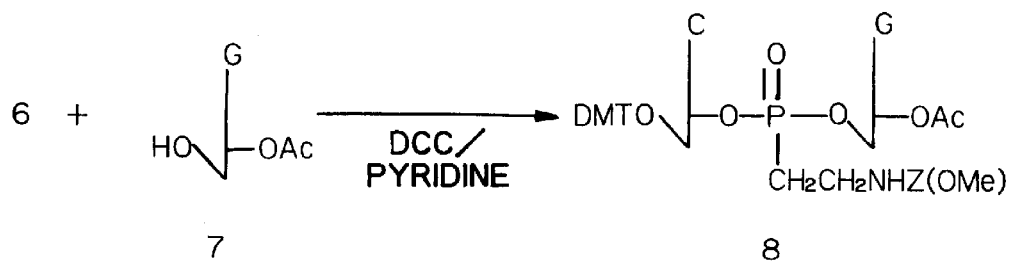
FIG. 7 shows a reaction scheme for the third stage of the preparation of YO-271 in Example 5.

In accordance with the reaction scheme shown in FIG. 7, Compound 6 (4 mmol) and Compound 7 (4 mmol) were dissolved in 40 ml of dry pyridine and DCC (20 mmol) was added to the solution, which was subjected to reaction at 45° C. for a day; the resulting dicyclohexylurea was filtered off the reaction solution to give Compound 8 (yield: 70%). In the scheme shown in FIG. 7, Ac designates a protective acetyl group.

Figure 8:
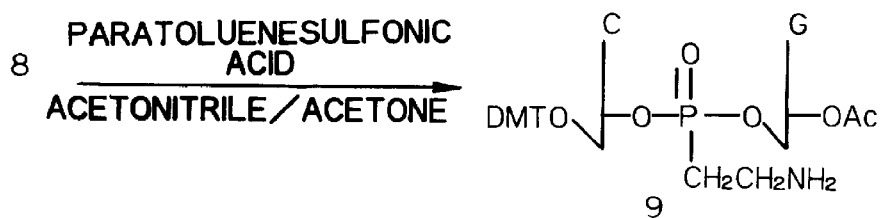
FIG. 8 shows a reaction scheme for the fourth stage of the preparation of YO-271 in Example 5.

In accordance with the reaction scheme shown in FIG. 8, Compound 8 (2.5 mmol) and partoluenesulfonic acid (5 mmol) were dissolved in 50 ml of an acetonitrile-acetone (1:1) mixture and the resulting solution was subjected to reaction at room temperature for a day to give Compound 9 (yield: 85%).

Figure 9:
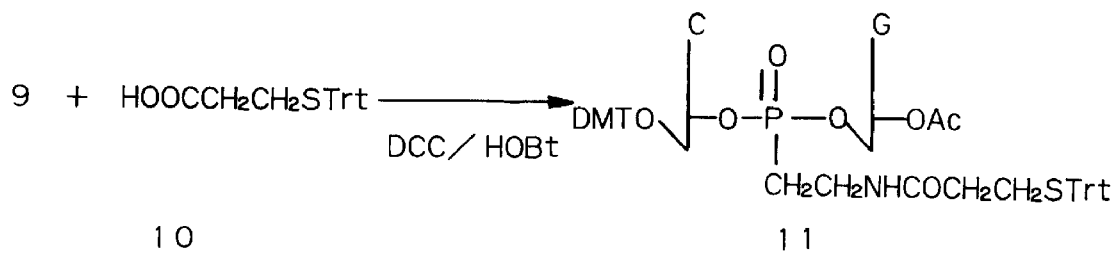
FIG. 9 shows a reaction scheme for the sixth stage of the preparation of YO-271 in Example 5.

In accordance with the reaction scheme shown in FIG. 9, a mixture of Compound 9 (2 mmol) and Compound 10 (2 mmol) in DMF (20 ml) was cooled to 0C, and DCC (2.4 mmol) and 4 mmol of 1-hydroxybenzotriazole (HOBt) were added to the solution. The mixture was subjected to reaction at 0° C. for 1 h, then at room temperature for another one hour. The resulting dicyclohexylurea was filtered off the reaction solution to give Compound 11 (yield: 80%). In the scheme shown in FIG. 9, Trt stands for a protective trityl group.

Figure 10:
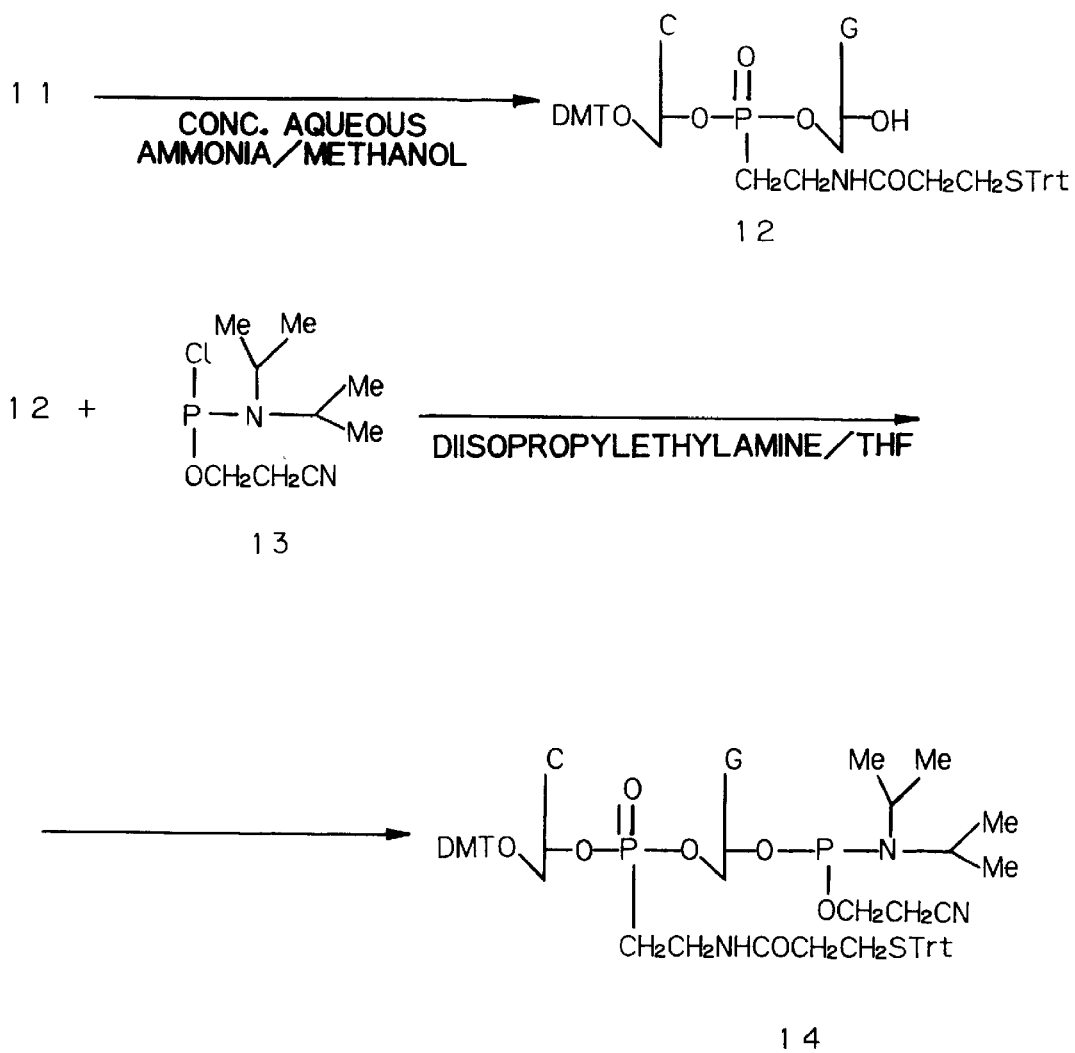
FIG. 10 shows a reaction scheme for the seventh stage of the preparation of YO-271 in Example 5.

In accordance with the reaction scheme shown in FIG. 10, Compound 11 (1 mmol) was dissolved in 50 ml of a mixture of methanol and conc. aqueous ammonia (1:1), and the resulting solution was subjected to reaction at room temperature for a day to give Compound 12, which was vacuum derived for thorough dehydration and dissolved in dry THF (10 ml); diisopropylethylamine (5 mml) and Compound 13 (5 mmol) were added to the resulting solution, which was subjected to reaction at room temperature for 1 h to give compound (yield: 80%).

Starting with Compound 14 as well as 3'-O-phosphoamidite type nucleoside containing A, T, G and C as bases, a probe oligonucleotide YPF-271 having the following base sequence was synthesized with a DNA synthesizer (391DNA Synthesizer of Applied Biosystems Inc.):

YPF-271: (5')CTCGC*GGGGGCTG(3')

where * indicates the position of a phosphate ester the phosphorus atom in which is modified as follows:

P—(CH$_2$)2—NH—CO—(CH$_2$)2—S—Trt

Figures 11, 12:
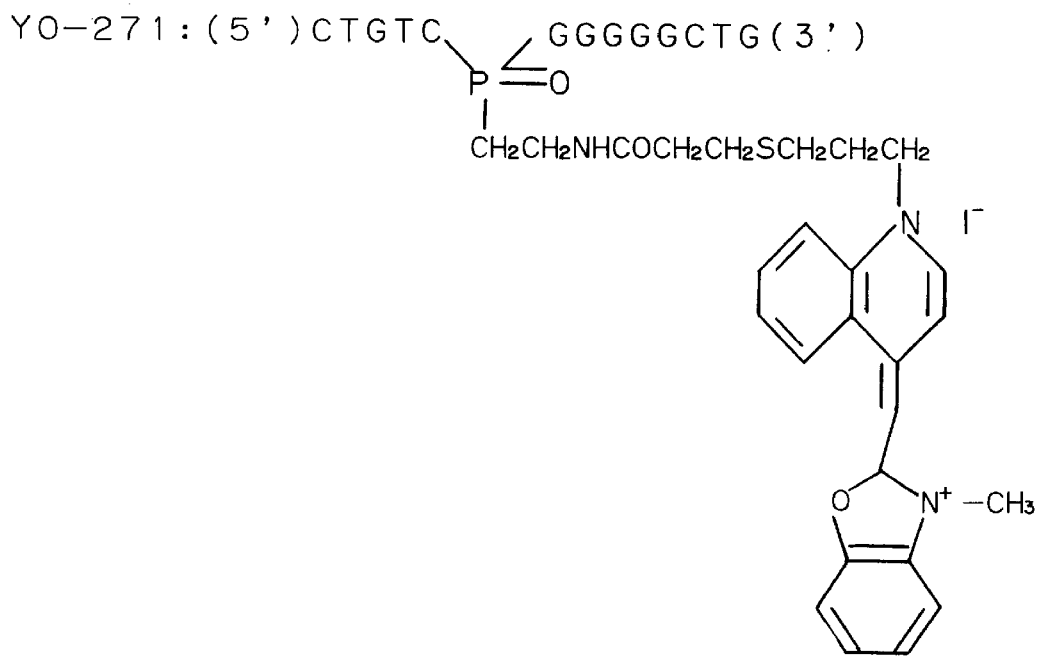
FIG. 11 shows a reaction scheme for the final stage of the preparation of YO-271 in Example 5.
FIG. 12 shows how Target Types 1 and 2, the oligonucleotides synthesized in Example 6, formed double strands with YO-271, the labeled nucleic acid probe prepared in Example 5.

The thus synthesized oligonucleotide YPF-271 was deprived of the trityl group in accordance with the procedure of Example 1 and reacted with Compound 8 to produce the labeled nucleic acid probe YO-271 represented by the formula shown in FIG. 11.

EXAMPLE 6

Experiment 4 for Detection of Target Nucleic Acid

Two target nucleotides, Target Types 1 and 2, were synthesized with a DNA synthesizer (391DNA Synthesizer of Applied Biosystems, Inc.); the respective nucleotides had the following base sequences:

Target Type 1:

(5')TTTGGGCGTGCCCCCGCAAGACTGCTAGCC(3')

Target Type 2:

(5')TTTGGGCGTGCCCCCGCGAGACTGCTAGCC(3')

The thus synthesized target oligonucleotides were such that a partly complementary double strand could be formed as shown in FIG. 12 with respect to the labeled nucleic acid probe YO-271 prepared in Example 5.

In FIG. 12, the asterisk "*" designates the labeled site of YO-271, the vertical bar "1" designates a complementary portion between YO-271 and Target Type 1 or 2, and "#" designates the site of a single base mismatch which occurs only between Target Type 1 and YO-271.

The labeled nucleic acid probe YO-271 (20 pmol) was mixed with 0, 5, 10, 20 or 30 pmol of Target Type 1 or 2 in 75 μl of 10 mM Tris-HCl (pH 8.3)/50 mM KCl/2.2 mM MgCl$_2$ and held at 50° C. for annealing. The intensities of fluorescence (510 nm) from the respective reaction solutions were measured at 50° C. with excitation of 488 nm.

Figure 13:
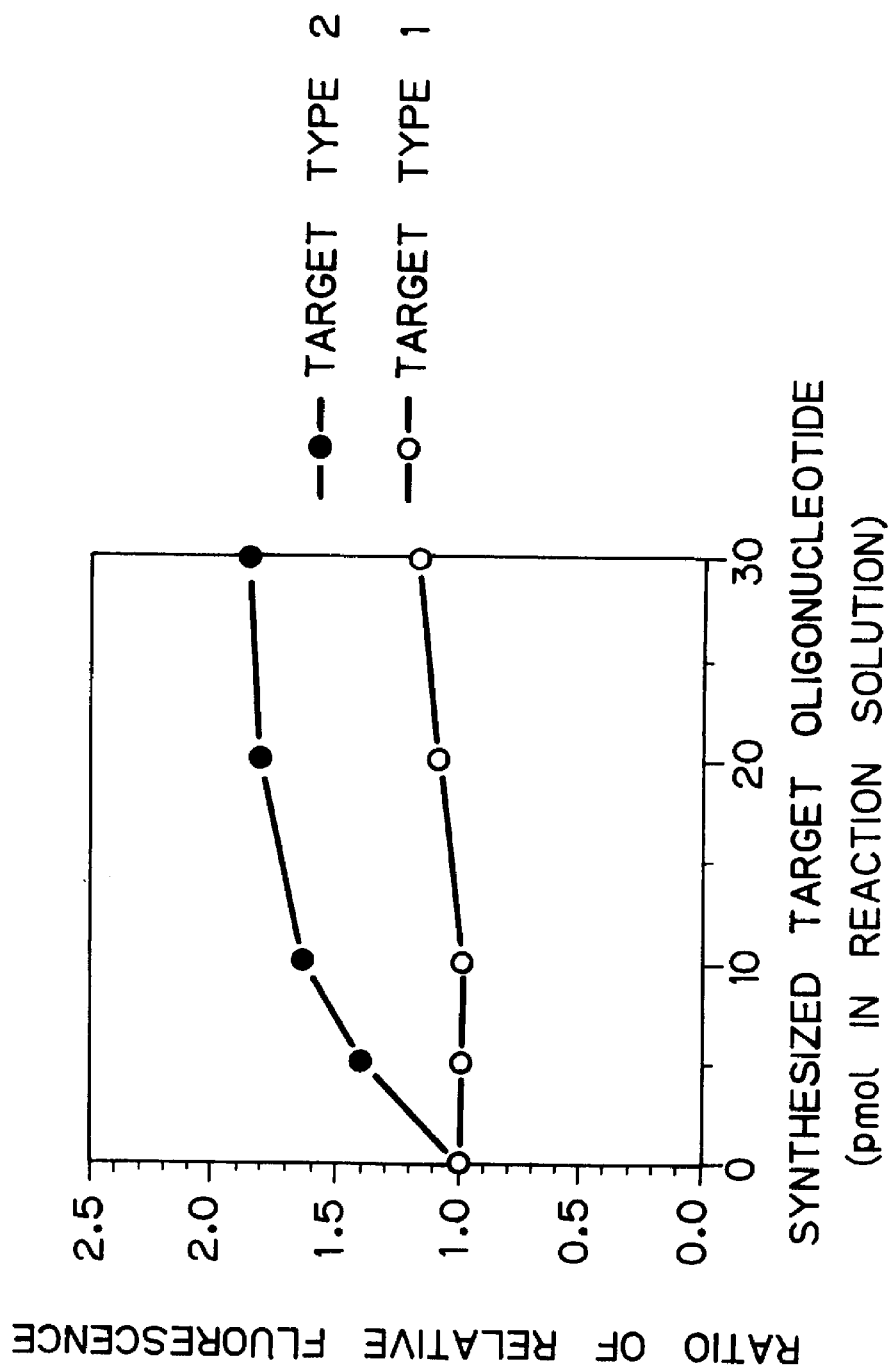
FIG. 13 is a graph showing the relative intensities of fluorescence from reaction solutions comprising 20 pmol of YO-271 and varying amounts of Target Type 1 or 2, with the value in the absence of target nucleic acids being taken as unity.

The results are shown in FIG. 13, from which one can see that the intensity of fluorescence increased with the amount of Target Type 2 in the reaction solution and saturated when its amount was 20 pmol (which was equal to the amount of YO-271). On the other hand, the intensity of fluorescence from the reaction solution hardly increased even when the amount of Target Type 1 was increased up to 30 pmol. Thus, it was verified that the labeled nucleic acid probe YO-271 could not only recognize the target nucleic acid (Target Type 2) in a dose-dependent manner but also identify the single base mismatch in that target nucleic acid.

EXAMPLE 7

Preparation of Target Nucleic Acid

Before amplifying the 5' non-coding region of hepatitis C virus (HCV) RNA, primers were provided by mechanically synthesizing the following oligonucleotides as in Example 6:

U25: (5')CTCCACCATAGATCACTCCCC(3')

L296: (5')GCACTCGCAAGCACCCTAT(3')

The pooled sera of American hepatitis C patients (100 μl) and that of Japanese hepatitis C patients (100 μl) were each treated with a TOSOH DNA/RNA EXTRACTION KIT (product of Tosoh Corp.) to extract HCV RNA and the extracted pellets were dissolved in 12 μl of TE [Tris-HCl (pH 8.0)/0.1 mM EDTA] containing 100 μg/ml of yeast RNA. The resulting HCV RNA solution (10 μl) was mixed with 5 μl of a reaction solution for reverse transcription and the mixture was subjected to the reaction of reverse transcription at 42° C. for 10 min in 15 μl of a reaction solution consisting of the following components: 10 mM Tris-HCl (pH 8.3); 50 mM KCl; 4.5 MM MgCl$_2$; 1.4 mM each of dNTPs; 1.1 U/μl of PNase Inhibitor (Takara Shuzo Co., Ltd.); 2 U/μl of MMLV Rtase (Life Technologies, Inc.); 1 mM DTT; and 1.2 μM L296 (all concentrations were final ones). After the reverse transcription reaction, heating was continued at 99° C. for 6 min to inactivate the reverse transcriptase.

The thus conditioned solution for reverse transcription (15 μl) was mixed with 60 μl of a solution for PCR reaction and the mixture was subjected to PCR reaction by repeating 40 temperature cycles, each consisting of heating at 95° C.×30 sec, 65° C.×30 sec and 72° C.×1 min, in 75 μl of a reaction solution consisting of the following components: 10 mM Tris-HCl (pH 8.3); 50 mM KCl; 2.2 mM MgCl$_2$; 0.28 mM each of dNTPs; 0.03 U/μl of Taq DNA Polymerase (Takara Shuzo Co., Ltd.); 1 mM DTT; 0.24 μM U25; and 0.24 μM L296 (all concentrations were final ones).

Thereafter, the PCR product was purified from the reaction solution by means of SpinBind DNA Extraction Units (Takara Shuzo Co., Ltd.) The purified pellets were each dissolved in 10 μl of TE and subjected to blunt end preparation by means of DNA Blunting Kit (Takara Shuzo Co., Ltd.) Thereafter, a phenol treatment and ethanol precipitation were performed by the usual procedures and the resulting precipitates were each redissolved in 10 μl of TE.

In a separate step, 2 μg of a commercial plasmid pBluescript IISK+ (Toyobo Co., Ltd.) was digested with a restriction enzyme HincII (Takara Shuzo Co., Ltd.) in a reaction buffer provided with the enzyme, followed by dephosphorylation with Calf Intestine Alkaline Phosphatase (Takara Shuzo Co., Ltd.). A phenol treatment and ethanol precipitation were conducted by the usual procedures and the resulting precipitate was redissolved in 10 μl of TE.

The thus prepared plasmid digest (1 μl) was mixed with 2 μl of the PCR product derived from the American or Japanese sera. Ligation was performed with DNA Ligation Kit (Takara Shuzo Co., Ltd.) for introduction into JM109 Component Cell (Takara Shuzo Co., Ltd.) and recombinant colonies were formed on an LB plate containing 50 μg/μl of ampicillin. The recombinant colonies were then cultured in an LB medium containing 50 μg/μl of ampicillin and a plasmid DNA was extracted by the usual procedure. By base sequencing with a Taq DyeDeoxy Terminator Cycle Sequencing Kit (product of ABI) and a DNA sequencer (373A of ABI), clones that agreed to the documented base sequence of HCV RNA were obtained for both the American and Japanese sera. The clone from the American sera was designated SKP/SC1-1 and the clone from the Japanese sera as SKP/SR1P2-6. Either clone had 290 bp of HCV RNA (base Nos. 25–314) inserted in the direction of transfer by T7 promoter in the plasmid pBluescript IISK+(the base numbers were in accordance with Choo, Q. et al., Proc. Natl, Acad. Sci. 88, pp. 2451–2455, 1991).

That region of the base sequence of either clone which corresponded to the target nucleic acid probe YO-271 prepared in Example 5 was capable of forming a partly complementary double strand as shown in FIG. 14.

In FIG. 14, the asterisk "*" designates the labeled site of YO-271, the vertical bar "|" designates a complementary portion between YO-271 and SKP/SC1-1 or SKP/SR1P2-6, and "#" designates the site of a single base mismatch which occurs only between SKP/SC1-1 and YO-271.

The clones SKP/SC1-1 and SKP/SR1P2-6 each weighing 1 mg were digested with a restriction enzyme HindIII in a reaction buffer provided with the enzyme. Thereafter, a phenol extraction and ethanol precipitation were conducted by the usual procedures and the resulting precipitate was redissolved in 500 pl of TE.

The HindIII digests of SKP/SC1-1 and SKP/SR1P2-6 each weighing 3 μl (ca. 6 μg) were reacted in 275 μl of a reaction solution at 37° C. for 1 h to effect in vitro RNA transfer. The reaction solution consisted of the following components: 40 mM Tris-HCl (pH 8.0); 8 mM MgCl$_2$; 2 mM spermidine; 5 mM DTT; 0.4 mM each of NTPs; 1 U/μl of RNase Inhibitor (Takara Shuzo Co., Ltd.); and 5 U/μl of T7 RNA polymerase (all concentrations were final ones). Thereafter, 28 μl of 1 mg/ml DNase I (Nakarai Tesk Co., Ltd.) was added and reaction was carried out at 37° C. for 30 min to degrade the template DNA, followed by the usual procedures of phenol extraction and ethanol precipitation. The resulting precipitate was redissolved in 250 μl of TE. The concentration of either RNA solution was estimated to be about 1012 molecules/pl on the basis of the light absorbance at a wavelength of 260 nm.

Each of these RNA solutions was diluted 107 and 109 folds with TE containing 100 μg/ml of yeast RNA to prepare target nucleic acid solutions at respective concentrations of ca. 105 and 103 molecules per microliter.

EXAMPLE 8

Experiment 5 for Detection of Target Nucleic Acid

Before amplifying the 5' non-coding region of HCV RNA, primers were provided by synthesizing the following oligonucleotides with a DNA synthesizer (391DNA Synthesizer of Applied Biosystems, Inc.):

U23: (5')CACTCCACCATAGATCACTCC(3')

L294: (5')ACTCGCAAGCACCCTATCA(3')

Three of the RNA solutions prepared in Example 7, one being derived from SKP/SC1-1 and having a concentration of 105 molecules per microliter and the others derived from SKP/SR1P2-6 and having concentrations of 103 and 105 molecules per microliter, were mixed (each in 10 μl) with 5 μl of a reaction solution for reverse transcription and each mixture was subjected to the reaction of reverse transcription at 42° C. for 10 min in 15 μl of a reaction solution consisting of the following components: 10 mM Tris-HCl (pH 8.3); 50 mM KCl; 4.5 mM MgCl$_2$; 1.4 mM each of dNTPs; 1.1 U/μl of RNase Inhibitor (Takara Shuzo Co., LTd.); 2 U/μl of MMLV RTase (Life Technologies, Inc.); 1 mM DTT; and 0.05 μM L294 (all concentrations were final ones). After the reverse transcription reaction, heating was continued at 99° C. for 6 min to inactivate the reverse transcriptase.

The thus conditioned solution for reverse transcription (15 μl) was mixed with 50 μl of a solution for PCR reaction which contained all necessary components except Taq DNA polymerase and the mixture was heated to 72° C. After mixing with 10 μl of a PCR enzyme solution heated to 72° C. (0.5 U/μl of Taq DNA polymerase available from Takara Shuzo Co., Ltd.), the mixture was subjected to asymmetric PCR reaction for overamplification of the (+) strand by repeating 50 temperature cycles, each consisting of heating at 95° C.×30 sec, 65° C.×30 sec and 72° C.×1 min, in 75 μl of a reaction solution consisting of the following components: 10 mM Tris-HCl (pH 8.3); 50 mM KCl; 2.2 mM MgCl$_2$; 0.28 mM each od dNTPs; 1 mM DTT; 0.5 μM U23;

0.01 μM L294 and 0.067 U/μl of Taq DNA polymerase (all concentrations were final ones).

After the end of the asymmetric PCR reaction, 5 μl of the reaction solution was subjected to 2% agarose gel electrophoresis and stained with 10 μg/ml of an ethidium bromide solution. Examination under near ultraviolet light showed that for all the RNA solutions tested, bands formed in the desired positions, thus verifying the occurrence of asymmetric PCR amplification.

Figure 15:
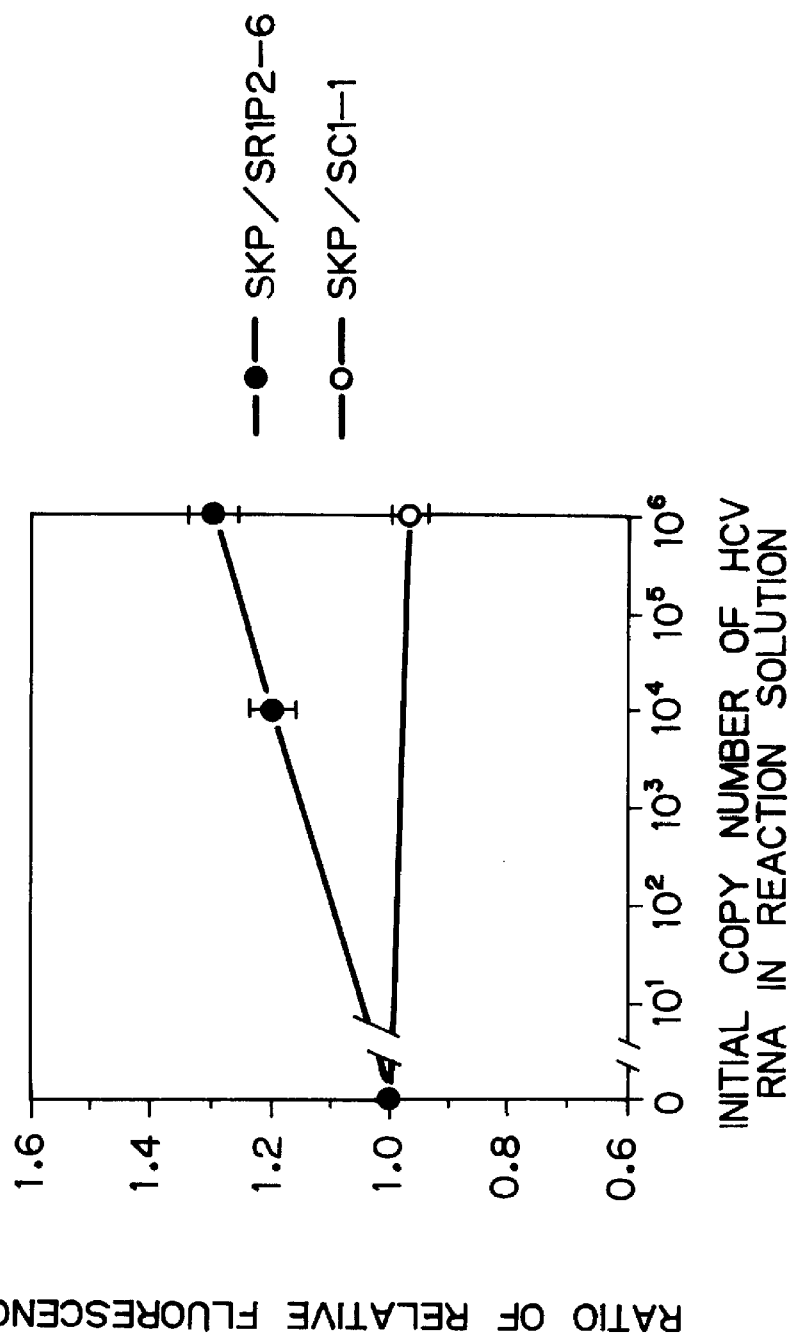
FIG. 15 is a graph showing the relative intensities of fluorescence from reaction solutions comprising 20 pmol of YO-271 and the (+) strand overamplified asymmetric PCR product of varying initial copy numbers, with the value in the absence of target nucleic acids being taken as unity.

A 10 mM Tris-HCl (pH 8.3)/50 mM KCl/2.2 mM $MgCl_2$ solution (10 μl) containing 20 pmol of the labeled nucleic acid probe YO-271 was mixed with 65 μl of each of solutions for asymmetric PCR reaction and, following heating at 99° C. for 6 min, the mixture was held at 45° C. for annealing. The intensities of fluorescence (510 nm) from the respective reaction solutions were measured at 45° C. with excitation at 488 nm. The results are shown in FIG. 15, from which one can see that the intensity of fluorescence increased for the (+) strand-rich asymmetric PCR product from the SKP/SR1P2-6 derived RNA. On the other hand, the intensity of fluorescence did not increase for the (+) strand-rich asymmetric PCR product from the SKP/SC1-1 derived RNA. Thus, it was verified that the labeled nucleic acid probe YO-271 could not only recognize the specific (+) strand-rich asymmetric PCR product but also identify the single base mismatch in that product.

EXAMPLE 9

Experiment 6 for Detection of Target Nucleic Acid

The two RNA solutions prepared in Example 7 as derived from SKP/SR1P-2, one having the concentration of 103 molecules/μl and the other 105 molecules/pl, were each metered in 10 μl and subjected to asymmetric PCR for over-amplification of the (+) strand as in Example 8, except that 20 pmol of YO-271 was added to a certain PCR reaction solution at the time of starting asymmetric PCR.

Similarly, 10 μl of the RNA solution derived from SKP/SR1P2-6 which had the concentration of 105 molecules/μl was subjected to asymmetric PCR for overamplification of the (−) strand as in Example 8. In this case, primer L294 was added to the RT reaction solution to give a final concentration of 2.5 μM (which would be 0.5 μM during PCR) and primer U23 was added at the time of starting PCR to give a final concentration of 0.01 μM, provided that 20 pmol of YO-271 was added to a certain PCR reaction solution at the time of starting asymmetric PCR.

After the end of each asymmetric PCR run, 5 μl of the reaction solution was subjected to 2% agarose gel electrophoresis and stained with 10 μg/ml of an ethidium bromide solution. Examination under near ultraviolet light showed that for all the RNA solutions tested, bands formed in the desired positions, thus verifying the occurrence of asymmetric PCR amplification.

In the case where the labeled nucleic acid probe YO-271 was not added at the time of starting asymmetric PCR, a 10 mM Tris-HCl (pH 8.3)/50 mM KCl/2.2 mM $MgCl_2$ solution (10 μl) containing 20 pmol of YO-271 was mixed with 65 μl of the solution for asymmetric PCR reaction and, following heating at 99° C. for 6 min, the mixture was held at 45° C. for annealing. In the case where YO-271 was added at the time of starting asymmetric PCR, a 10 mM Tris-HCl (pH 8.3)/50 mM KCl/2.2 mM $MgCl_2$ solution (10 μl) was mixed with 65 μl of the solution for asymmetric PCR reaction and the mixture was similarly annealed. The intensities of fluorescence (510 nm) from the respective reaction solutions were measured at 45° C. with excitation at 488 nm.

Figure 16:
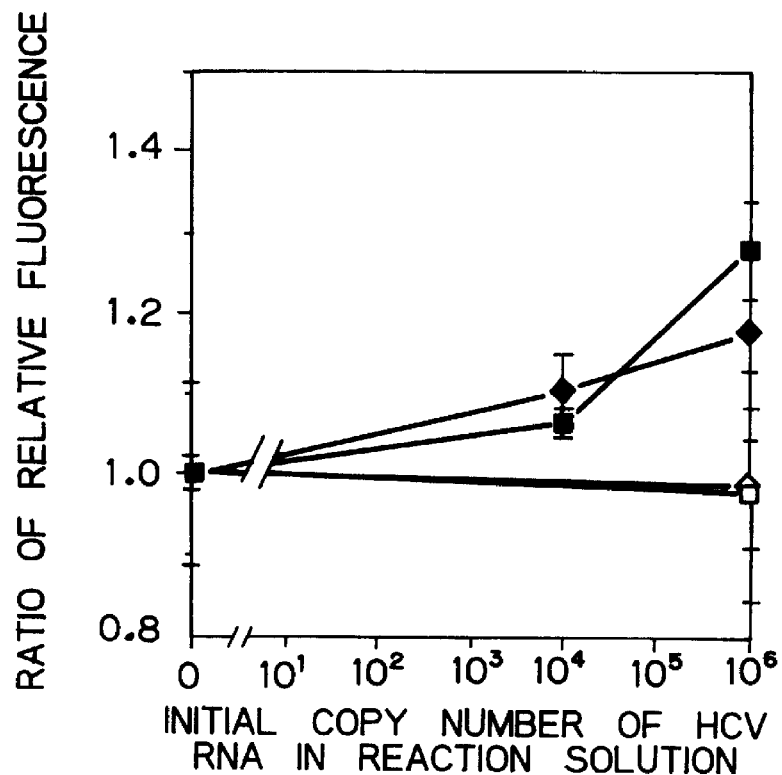
FIG. 16 is a graph showing the relative intensities of fluorescence from reaction solutions comprising 20 pmol of YO-271 and the (+) or (−) strand overamplified asymmetric PCR product of varying initial copy numbers, with YO-271 being added either at the start or end of asymmetric PCR and with the value in the absence of target nucleic acids being taken as unity.

The results are shown in FIG. 16, from which one can see that in the case where the labeled nucleic acid probe YO-271 was not added at the time of starting asymmetric PCR, the intensity of fluorescence increased for the (+) strand over-amplified asymmetric PCR product from the SKP/SR1P2-6 derived RNA but did not increase for the (−) strand over-amplified asymmetric PCR product. Thus, it was verified that the labeled nucleic acid probe YO-271 could recognize the specific asymmetric PCR product. FIG. 16 also shows that the same results were obtained when YO-271 was added at the time of starting asymmetric PCR. IT was thus verified that the procedures of post-treatment for the detection of a specific asymmetric PCR product could be simplified by adding the labeled nucleic acid probe YO-271 at the time of starting asymmetric PCR.

EXAMPLE 10

Monitoring the Quantity of Transfer Product in In Vitro Transfer System

The SKP/SR1P2-6 constructed in Example 7 was cleaved with restriction enzymes to prepare linear DNAS, which were used as template DNAs for in vitro transfer.

Figure 17:
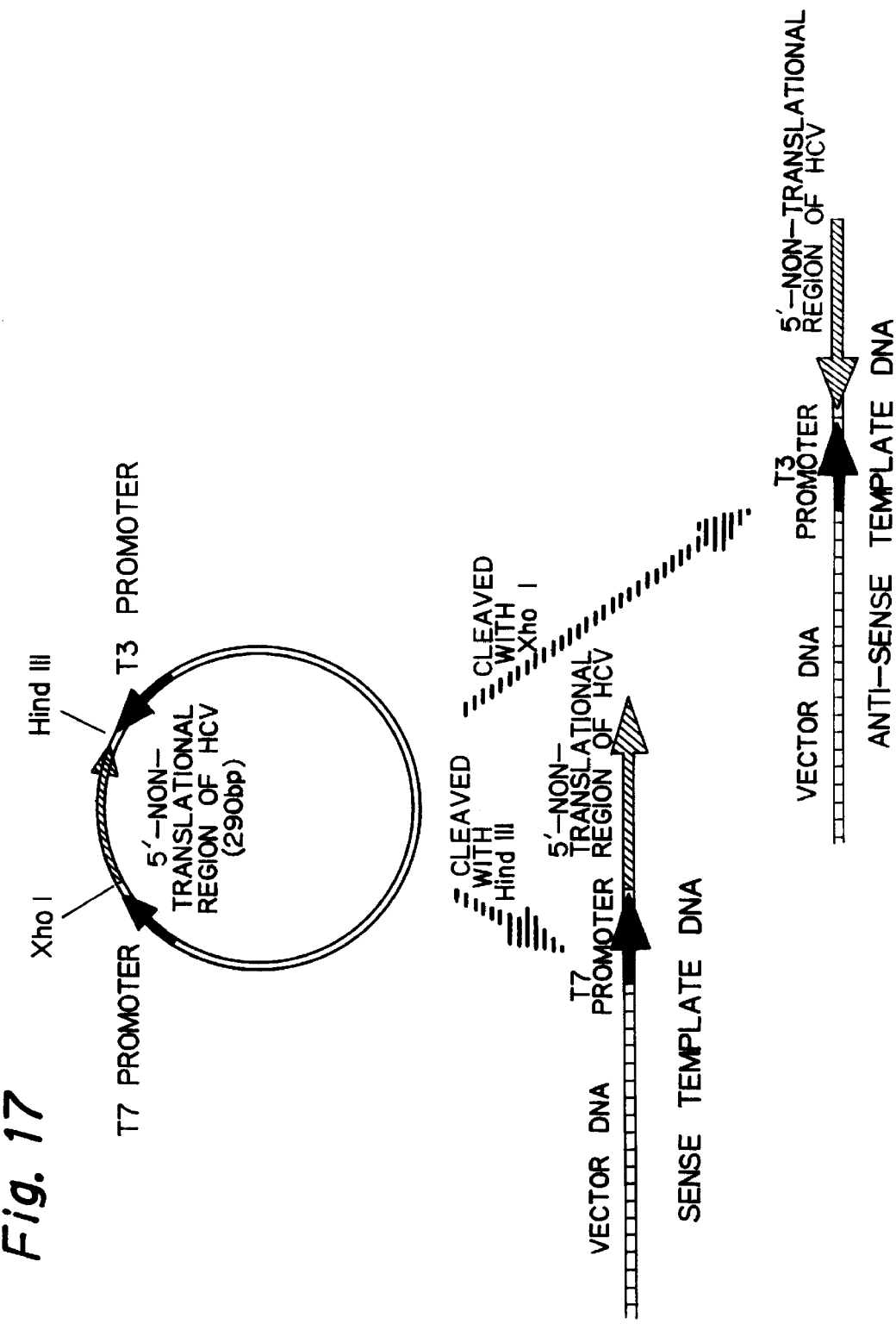
FIG. 17 shows the structures of sense and anti-sense linear template DNAs as cleaved from SKP/SR1P2-6 with different restriction enzymes.

The structures of the thus prepared linear DNAs are shown in FIG. 17; the linear DNA obtained by cleavage with HindIII was used as a template for transfer from T7 promoter and the one obtained by XhoI was used as a template for transfer from T3 promoter. Reaction solutions (500 μl) containing the respective template DNAs and having the composition set forth below were each charged into a fluorometric cell and subjected to reaction at 40° C. in a spectrophotofluorimeter.

| Reaction Solution | |
|---|---|
| 40 mM | Tris-HCl (pH 8.0) |
| 8 mM | $MgCl_2$ |
| 5 mM | DTT |
| 0.4 mM | dNTPs |
| 7 nM | template DNA (sense or anti-sense) |
| 25 nM | YO-271 |
| 2 U/μl | RNase inhibitor |
| 0.1 U/μl | T7 RNA polymerase or T3 RNA polymerase |

Figure 18:
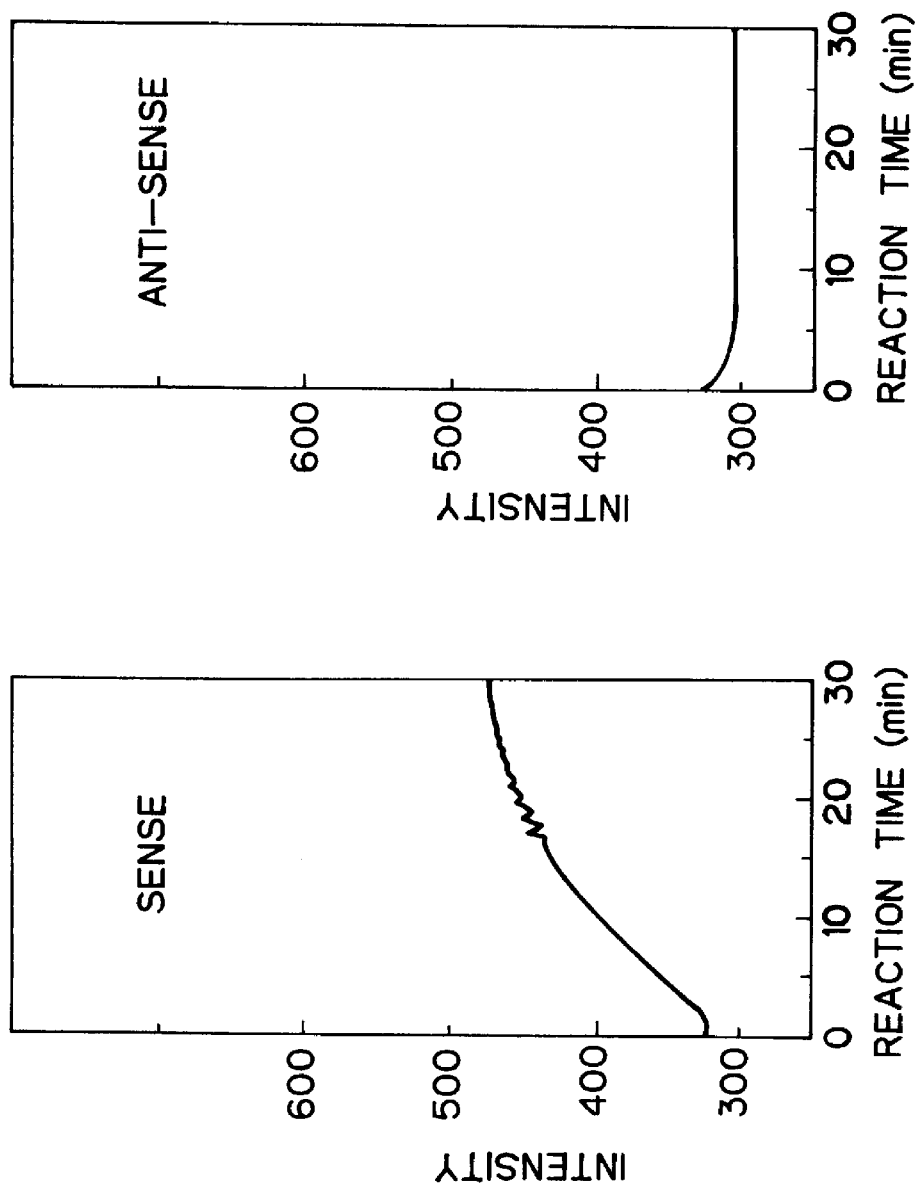
FIG. 18 shows the results of spectrophotofluorimetry of reaction solutions containing the sense and anti-sense templates.
Figure 19:
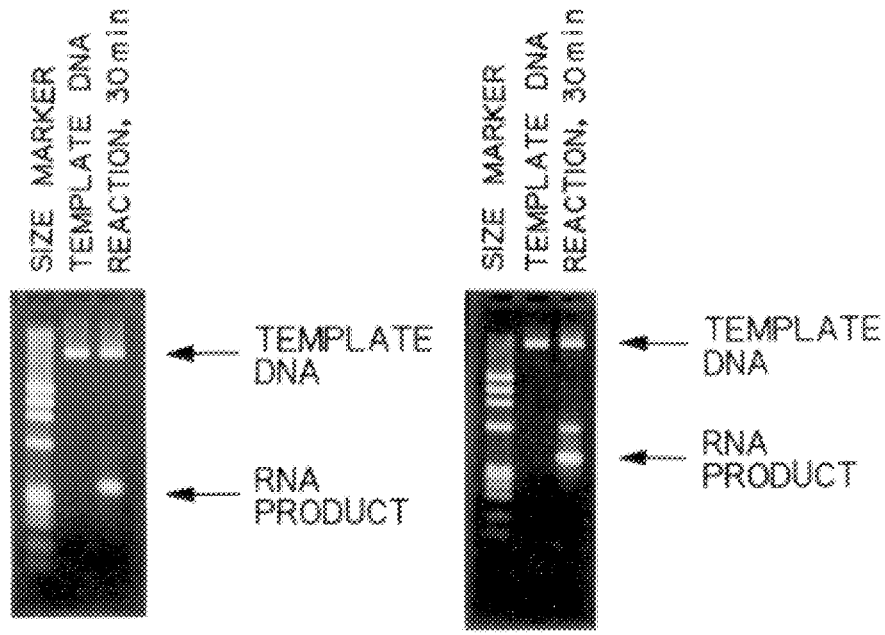
FIG. 19 shows the results of electrophoresis of the sense and anti-sense transfer products in which φX174/Hae III was used as a size marker.

As soon as the reaction started, fluorescing at 510 nm was monitored (excitation wavelength: 490 nm) for 30 min and the results are shown in FIG. 18. After the reaction, 10 μl of each transfer product was subjected to electrophoresis and the results are shown in FIG. 19. The transfer product was generated in both cases but fluorescence was detected only in the case of sense template DNA. From these results, one may safely conclude that the use of the labeled nucleic acid probe YO-271 enables the measurement of transfer products in a specific manner.

Figure 20:
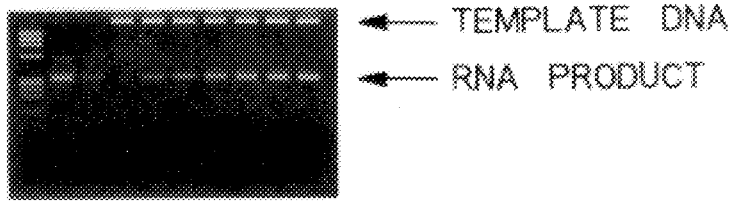
FIG. 20 shows the time profile of electrophoresis of the transfer product from reaction solutions containing T7 RNA polymerase and sense template, in which the control RNA was purified from the same RNA as the transfer product and determined for its density from the absorbance at 260 nm and in which φX174/Hae III was used as a size marker.
Figure 21:
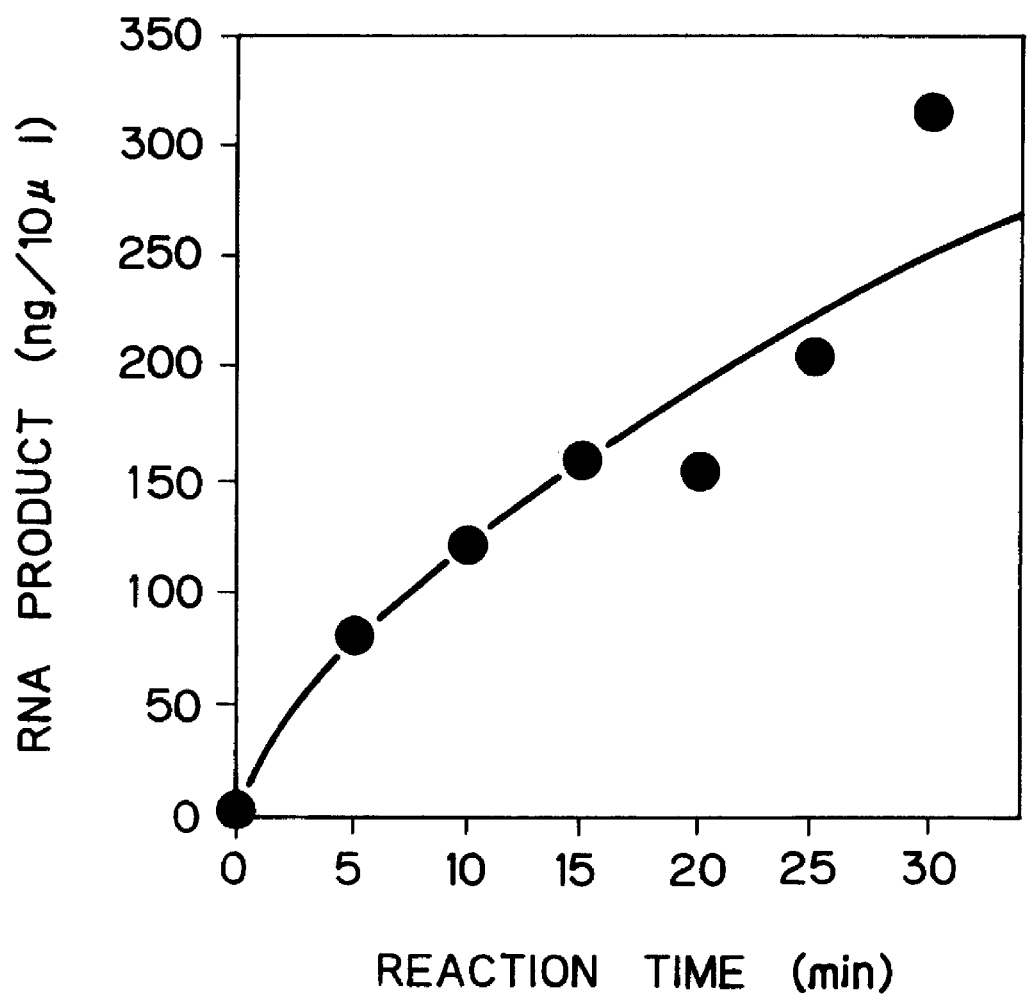
FIG. 21 shows the result of densitometry of the bands forming in FIG. 20, as compared with the control RNA.

In another run that was performed under the same reaction conditions using T7 RNA polymerase and sense template DNA, 10 μl of the reaction solution was sampled at given time intervals and subjected to electrophoresis. The result is shown in FIG. 20. The densities of the band shown in FIG. 20 were measured with a densitometer and the results are shown in FIG. 21. The reaction curve in the graph on the left side of FIG. 18 correlates well with the curve in FIG. 21, thus verifying the emission of fluorescence in proportion to the amount of the RNA product. These results demonstrate that the assay system of the invention enables the RNA product to be quantitated in a specific manner without recovering the sample of interest.

As will be apparent from the foregoing description, the present invention provides a convenient, single-stage method in a homogeneous system by which a target nucleic acid having at least one specific nucleic acid sequence that is contained in a sample of interest suspected to comprise a gene mixture can be detected and quantitated without the need to analyze the reaction solution after PCR-based amplification or separate the excess probe which has not participated in the formation of a complementary bond. Therefore, the present invention enables convenient detection of target nucleic acids in various gene-related fields such as gene diagnosis, the cloning of useful genes and the search for unknown genes. The invention also enables optimization of the reaction conditions such as cycle time for the PCR-related amplification.

When the labeled nucleic acid probe of the invention forms a complementary bond with the target nucleic acid, the intercalating fluorochrome bound to the probe emits an increased intensity of fluorescence. If this phenomenon is utilized, the occurrence of complementary binding can be detected and the quantity of the resulting complementary binding product can be determined without requiring any extra step such as for separating the excess probe which did not participate in the formation of the complementary bond. Hence, the invention provides a convenient, one-stage method by which a nucleic acid comprising a specific nucleic acid sequence can be assayed in a homogeneous system. It should particularly be noted that the method of the invention which does not have to use an insoluble carrier is free from any of the associated problems such as non-specific adsorption of the labeled nucleic acid probe onto the insoluble carrier.

Another advantage of the invention is that if the labeled nucleic acid probe is added to the sample of interest prior to PCR amplification of the target nucleic acid, the time profile of its amplification can be monitored by measuring the intensity of fluorescence from the reaction solution during amplification. Therefore, the detection and quantification of the target nucleic acid in the sample before amplification can be accomplished without analyzing the reaction solution after amplification.

The Applicants previously invented a method of performing PCR in the presence of a free intercalating fluorochrome (Japanese Patent Public Disclosure No. 237000/1993) but, in that method, background fluorescence increased due to the non-specific intercalation of the fluorochrome into a double-stranded nucleic acid. This problem is eliminated from the present invention since the labeled nucleic acid probe it uses imparts "specificity" to the intercalating fluorochrome which is used as the marker.

What is claimed is:

1. In a method of assaying a target nucleic acid, or a nucleic acid in a sample of interest that has at least one specific nucleic acid sequence, said method using as a probe a single-stranded oligonucleotide having a nucleic acid sequence complementary to said specific nucleic acid sequence in the target nucleic acid and including the step of adding the probe to the sample such as to form a complementary bond with the target nucleic acid, the improvement wherein said probe is a single-stranded oligonucleotide labeled with an intercalating fluorochrome which is to be intercalated into the complementary binding portion between the target nucleic acid and the single-stranded oligonucleotide probe, wherein said probe and said target nucleic acid are not bound to a solid support.

2. In a method of assaying a target nucleic acid, or a double-stranded nucleic acid in a sample of interest that has at least one specific nucleic acid sequence, said method using as a probe a single-stranded oligonucleotide having a nucleic acid sequence complementary to said specific nucleic acid sequence in the target nucleic acid and including the step of adding the probe to the sample such as to form a triple-stranded nucleic acid with the target nucleic acid, the improvement wherein said probe is a single-stranded oligonucleotide labeled with an intercalating fluorochrome which is to be intercalated into the triple-stranded portion formed from the target nucleic acid and the single-stranded oligonucleotide probe, wherein said probe and said target nucleic acid are not bound to a solid support.

3. A method according to claim 1, wherein said intercalating fluorochrome has such a property that a fluorescence characteristic thereof will change when it is intercalated into the complementary binding portion between the target nucleic acid and the single-stranded oligonucleotide probe.

4. A method according to claim 2, wherein said intercalating fluorochrome has such a property that a fluorescence characteristic thereof will change when it is intercalated into the triple-stranded portion formed from the double-stranded target nucleic acid and the improvement wherein said probe is a single-stranded oligonucleotide labeled with an intercalating fluorochrome which is to be intercalated into the triple-stranded portion formed from the target nucleic acid and the single-stranded oligonucleotide probe.

5. In a method of assaying a target nucleic acid, or a nucleic acid in a sample of interest that has at least one specific nucleic acid sequence, which method includes the step of amplifying at least said specific nucleic acid sequence portion, said method using as a probe a single-stranded oligonucleotide having a nucleic acid sequence complementary to said specific nucleic acid sequence in the target nucleic acid and further including the step of adding the probe to the sample such as to form a complementary bond with the target nucleic acid, the improvement wherein said probe is a single-stranded oligonucleotide labeled with an intercalating fluorochrome which is to be intercalated into the complementary binding portion between the target nucleic acid and the single-stranded oligonucleotide probe, wherein said probe and said target nucleic acid are in solution not bound to a solid support.

6. In a method of assaying a target nucleic acid, or a double-stranded nucleic acid in a sample of interest that has at least one specific nucleic acid sequence, which method includes the step of amplifying at least said specific nucleic acid sequence portion, said method using as a probe a single-stranded oligonucleotide having a nucleic acid sequence complementary to said specific nucleic acid sequence in the target nucleic acid and further including the step of adding the probe to the sample such as to form a complementary bond with the target nucleic acid, the improvement wherein said probe is a single-stranded oligonucleotide labeled with an intercalating fluorochrome which is to be intercalated into the triple-stranded portion formed from the target nucleic acid and the single-stranded oligonucleotide probe, wherein said probe and said target nucleic acid are not bound to a solid support.

7. A method according to claim 5 or 6, wherein the single-stranded oligonucleotide probe is added to the sample prior to the step of amplifying the specific nucleic acid sequence portion.

8. A method according to claim 5 or 6, wherein the step of amplifying the specific nucleic acid sequence portion is performed by a PCR (polymerase chain reaction) technique.

* * * * *